(12) United States Patent
Winter

(10) Patent No.: US 10,820,836 B2
(45) Date of Patent: Nov. 3, 2020

(54) FOOT STRIKE ANALYZER SYSTEM AND METHODS

(71) Applicant: ShoeSense, Inc., Centennial, CO (US)

(72) Inventor: Connor Robert Winter, Centennial, CO (US)

(73) Assignee: ShoeSense, Inc., Centennial, CO (US)

( * ) Notice: Subject to any disclaimer, the term of this patent is extended or adjusted under 35 U.S.C. 154(b) by 45 days.

(21) Appl. No.: 15/618,060

(22) Filed: Jun. 8, 2017

(65) Prior Publication Data

US 2017/0354348 A1 Dec. 14, 2017

Related U.S. Application Data

(60) Provisional application No. 62/347,522, filed on Jun. 8, 2016.

(51) Int. Cl.
| | | |
|---|---|---|
| *A61B 5/103* | (2006.01) | |
| *A61B 5/00* | (2006.01) | |
| *G01L 5/00* | (2006.01) | |
| *G01P 13/00* | (2006.01) | |
| *A61B 5/11* | (2006.01) | |
| *G06F 30/20* | (2020.01) | |

(Continued)

(52) U.S. Cl.
CPC ............ *A61B 5/1038* (2013.01); *A61B 5/112* (2013.01); *A61B 5/1123* (2013.01); *A61B 5/6807* (2013.01); *G01L 5/0052* (2013.01); *G01P 13/00* (2013.01); *G06F 30/20* (2020.01); *A43B 3/0005* (2013.01); *A43B 3/0031* (2013.01); *A43B 5/00* (2013.01); *A43B 5/06* (2013.01); *A43B 7/00* (2013.01); *A61B 5/6829* (2013.01); *A61B 2503/12* (2013.01); *A61B 2562/0219* (2013.01); *A61B 2562/04* (2013.01); *G06F 2113/12* (2020.01)

(58) Field of Classification Search
CPC ..... A61B 5/1038; A61B 5/112; A61B 5/1123; A61B 5/6807; A61B 2503/12; A61B 2562/0219; A43B 3/0005; A43B 3/0031; A43B 5/06; A43B 7/00; G01L 5/0052; G01P 13/00; G06F 17/5009; G06F 2217/32

See application file for complete search history.

(56) References Cited

U.S. PATENT DOCUMENTS

| | | | | | |
|---|---|---|---|---|---|
| 5,473,518 | A | * | 12/1995 | Haber | ................ A43B 1/0072 36/137 |
| 5,955,667 | A | * | 9/1999 | Fyfe | .................... A43B 3/0005 702/160 |

(Continued)

OTHER PUBLICATIONS

PowerSpurz_Public Sale Evidence_2014.*

*Primary Examiner* — Sean P Dougherty
(74) *Attorney, Agent, or Firm* — Lathrop GPM LLP

(57) ABSTRACT

Systems, methods, and software products analyze foot strikes. A runner profile defining characteristics of a user and a shoe type of the shoes is received. Shoe characteristics are retrieved based upon the shoe type. A model of shoe wear is configured based upon both the runner profile and the shoe characteristics. Sensor data indicative of movement of a runner's foot is received from a foot strike monitor configured with the shoes and processed through the model to determine a user's expected lifetime for the shoes. The user's expected lifetime is indicated to the user.

12 Claims, 25 Drawing Sheets

(51) Int. Cl.
    *A43B 3/00*     (2006.01)
    *A43B 5/06*     (2006.01)
    *A43B 7/00*     (2006.01)
    *G06F 113/12*     (2020.01)
    *A43B 5/00*     (2006.01)

(56) References Cited

U.S. PATENT DOCUMENTS

| | | | |
|---|---|---|---|
| 7,911,339 B2 | 3/2011 | Vock et al. | |
| 9,642,415 B2* | 5/2017 | Pease | G01C 22/006 |
| 10,363,453 B2* | 7/2019 | Fitzgerald | A61B 5/486 |
| 2007/0271826 A1* | 11/2007 | Mirza | A43B 1/0036 |
| | | | 36/137 |
| 2009/0278707 A1* | 11/2009 | Biggins | A43B 1/0027 |
| | | | 340/870.16 |
| 2012/0015779 A1* | 1/2012 | Powch | A61B 5/02055 |
| | | | 482/9 |
| 2014/0062703 A1* | 3/2014 | Purks | A61B 5/1122 |
| | | | 340/573.1 |
| 2014/0343460 A1* | 11/2014 | Evans, III | A61B 5/112 |
| | | | 600/595 |
| 2015/0032033 A1* | 1/2015 | Kaufman | A61B 5/726 |
| | | | 600/595 |
| 2015/0339726 A1* | 11/2015 | Herring | G06Q 30/0269 |
| | | | 705/14.58 |
| 2016/0067584 A1* | 3/2016 | Giedwoyn | A61B 5/112 |
| | | | 700/91 |
| 2016/0100801 A1* | 4/2016 | Clark | A61B 5/6807 |
| | | | 73/865.4 |
| 2017/0189752 A1* | 7/2017 | Mohrman | G01C 21/16 |

\* cited by examiner

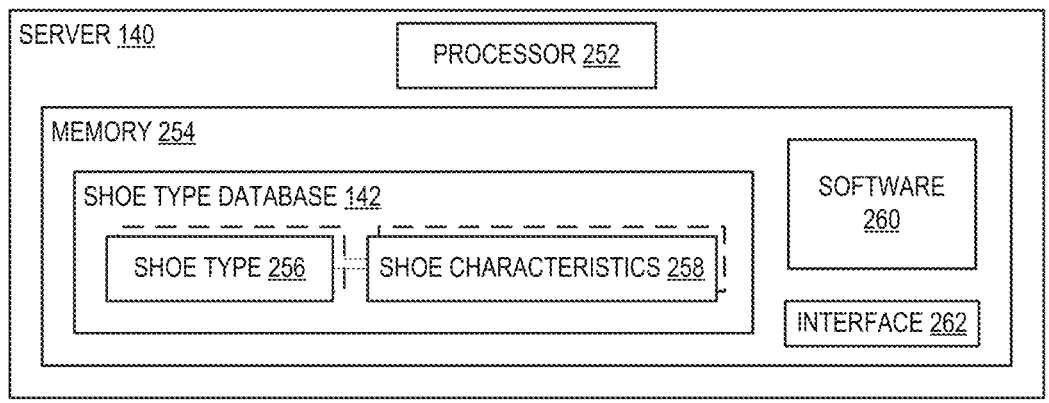
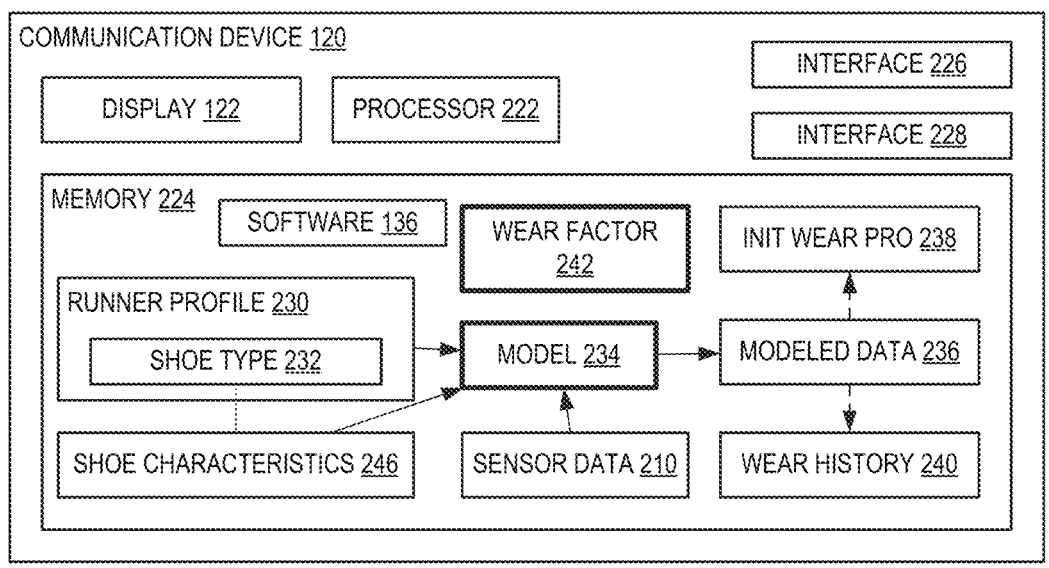
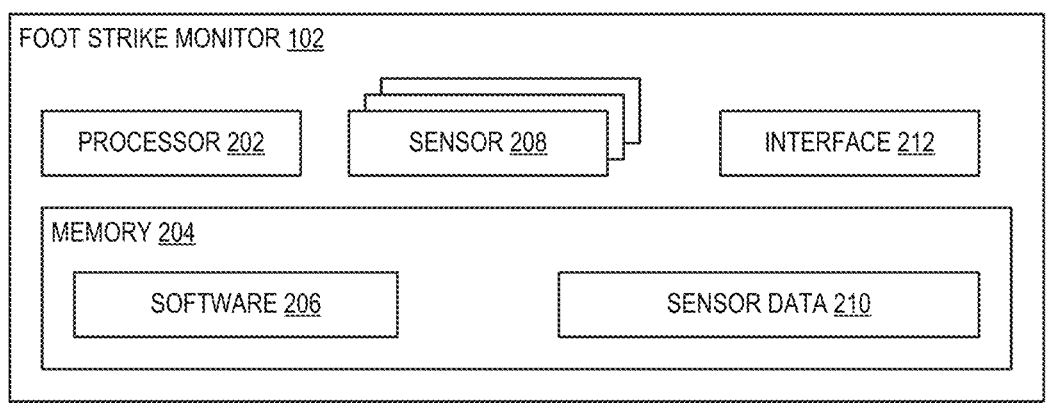
FIG. 2

```
MODEL 234
  FOOT STRIKE DETECTION ALGORITHM 1602
  MAX IMPACT FORCE ALGORITHM 1604
  PRONATION EXCURSION ANGLE ALGORITHM 1606
```

FOOT STRIKE ANALYZER SYSTEM AND METHODS

RELATED APPLICATIONS

This application claims priority to U.S. Patent Application Ser. No. 62/347,522, filed Jun. 8, 2016, and titled "Foot Strike Analyzer System and Methods," which is incorporated herein by reference.

BACKGROUND

Runners have no way of accurately knowing when their shoes are worn out. When a shoe is worn out it no longer gives the support and cushioning needed to prevent injuries. Typically, a new running shoe is given a 300-500 mile life recommendation. Thus, the most common way for the runner to know if their shoes are worn out is to visually inspect the shoe to see if they look worn or wait until the shoes hurt to run in. Alternatively, based upon the life recommendation of 300-500 miles, the runner estimates the distance run in the shoes and buys new shoes when the estimated distance is between 300 and 500 miles, or greater. However, many runners do not accumulate distance run in their shoes, or estimate the distance poorly, and frequently run in worn out shoes that result in injury to the runner's feet. Further, tracking distance run does not take into account the individual wear characteristics imparted to the shoes by each runner.

When a shoe is worn out it no longer provides the support and cushioning for the runner's lower extremities. Often times, when the shoe foam is worn out, the runner is unaware due to the fact that there is no way to accurately diagnose that the foam is broken down, other than an eye test and at the this point the runner may have already been at risk for injury for quite some time. As the runner continues to use the worn-out shoes, the runner's body is experiencing more force than it can handle. Over time the forces that used to be absorbed by the foam are now transmitted into the runner's body. This increased force then leads to injuries such as stress fractures in the bones, which can take many months of recuperation.

SUMMARY

In one embodiment, a system analyzes foot strikes and includes a foot strike monitor, configurable with a running shoe, for detecting movement of a runner's foot within the running shoe, an app, for downloading to, and executing on, a communication device. The app, when executed on the communication device receives the detected movement from the foot strike analyzer, models wear on the shoe based upon characteristics of the runner and characteristics of the shoe to determine a performance of the shoe, predicts a date when the performance of the shoe will fall below a defined threshold, and alerts the runner to the predicted date.

In another embodiment, a method analyzes foot strikes. A runner profile defining characteristics of a user and a shoe type of the shoes is received. Shoe characteristics are retrieved based upon the shoe type. A model of shoe wear is configured based upon both the runner profile and the shoe characteristics. Sensor data indicative of movement of a runner's foot is received from a foot strike monitor configured with the shoes and processed through the model to determine a user's expected lifetime for the shoes. The user's expected lifetime is indicated to the user.

In another embodiment, a method analyzes foot strikes. A runner profile defining a shoe type is received. Shoe characteristics are retrieved based upon the shoe type. A model of shoe wear is configured based upon both the runner profile and the shoe characteristics. Sensor data indicative of movement of a runner's foot is received from a foot strike monitor configured with a shoe and processed through the model during a first period to generate model data indicative of an initial performance of the shoe. The sensor data is processed through the model during a subsequent second period to generate model data indicative of a current performance of the shoe. The current performance and the initial performance are analyzed to determine change in performance of the shoe. A date when performance of the shoe will fall below a defined threshold is predicted and the runner is alerted to the predicted date.

In another embodiment, a software product has instructions, stored on non-transitory computer-readable media, wherein the instructions, when executed by a digital processor, perform steps for analyzing foot strikes, including instructions for configuring a model of shoe wear based upon both a runner profile and shoe characteristics, instructions for sensing, using at least one accelerometer configured with a shoe, sensor data indicative of movement of a runner's foot, instructions for processing the sensor data through the model during a first period to generate model data indicative of an initial performance of the shoe, instructions for processing the sensor data through the model during a subsequent second period to generate model data indicative of a current performance of the shoe, instructions for analyzing the current performance and the initial performance to determine change in performance of the shoe, instructions for predicting a date when performance of the shoe will fall below a defined threshold, and instructions for alerting the runner to the predicted date.

BRIEF DESCRIPTION OF THE FIGURES

FIG. 2 shows foot strike analyzer of FIG. 1 in further example detail.

DETAILED DESCRIPTION OF THE EMBODIMENTS

Figure 1:
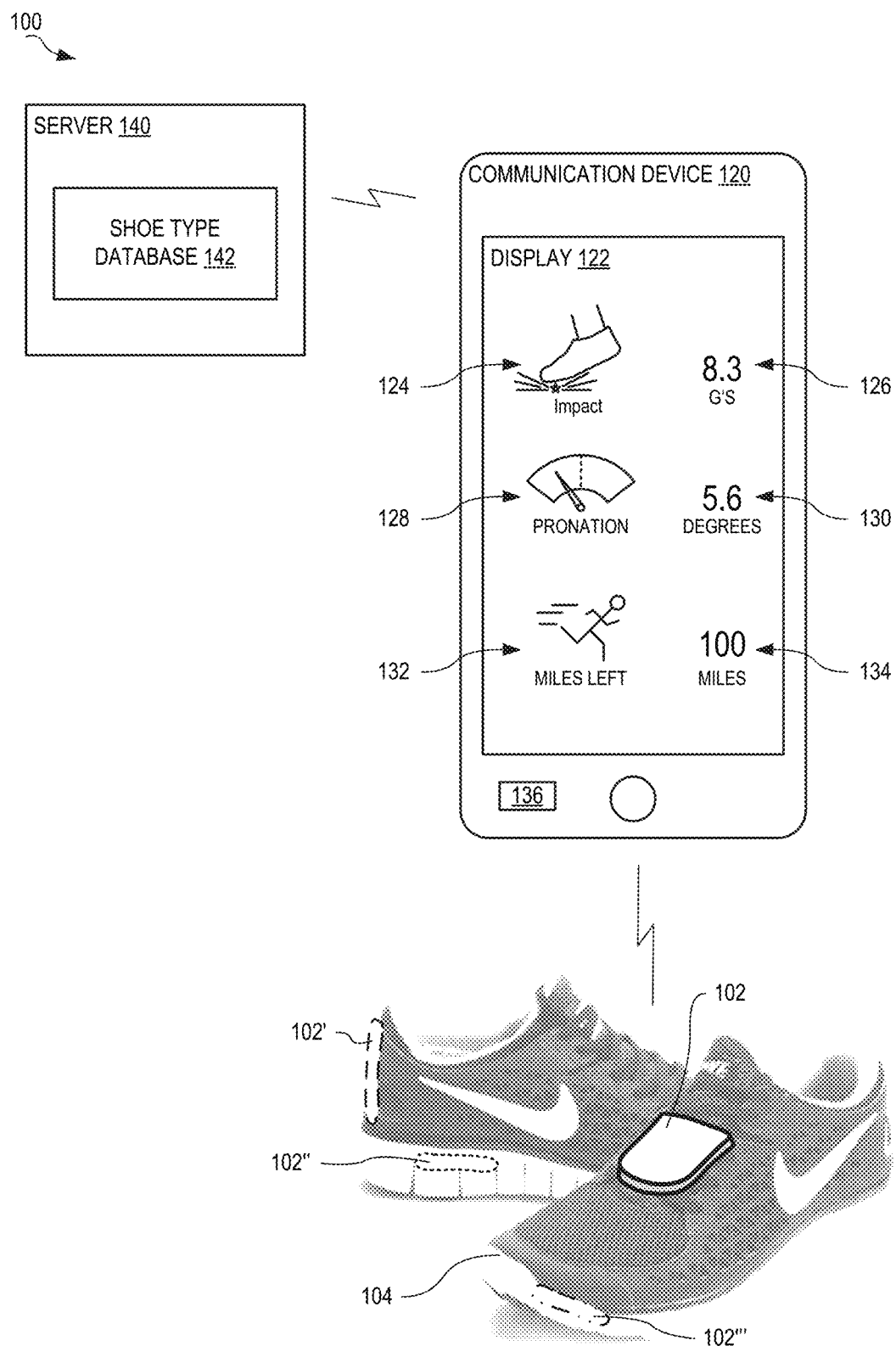
FIG. 1 shows one example foot strike analyzer for monitoring and displaying force experienced through a running shoe, in an embodiment.

FIG. 1 shows one example foot strike analyzer 100 having a foot strike monitor 102 that communicates with a communication device 120 (e.g., a smart phone or similar device) that cooperate to monitor the force being experienced through a running shoe 104 worn by the runner. As shown in FIG. 1, foot strike monitor 102 may attach (e.g., using the shoelaces) to an upper portion of running shoe 104. In an alternative embodiment, foot strike monitor 102 may attach, or be built into, a rear portion of the upper of shoe 104, illustrated as foot strike monitor 102'. In another embodiment, foot strike monitor 102 may be built into a heel of the sole of shoe 104, illustrated as foot strike monitor 102". In another embodiment, foot strike monitor 102 may be built into a forward part of the sole of shoe 104, illustrated as foot strike monitor 102'''. The sensor 102 may be permanently attached to the shoe or temporarily attached to the shoe. The permanent and temporary attachments are shown in the "Attachment and Sensor Design" document.

Foot strike monitor 102 senses acceleration and rotation experienced by running shoe 104, and hence experienced by a foot of the runner. Foot strike monitor 102 sends captured sensor data corresponding to the acceleration and rotation to communication device 120, where software 136 (e.g., an App) running on communication device 120 analyzes the data and determines impact, indicated by impact icon 124 and impact value 126, pronation, indicated by pronation icon 128 and pronation angle 130, and a wear indication, indicated by wear icon 132 and wear value 134. In the example of FIG. 1, wear value 134 indicates an estimated number of running miles remaining for running shoe 104 before cushioning and support degrades to a point where injury to the runner's foot may occur. Impact value 126, pronation angle 130, and wear value 134 may be color coded, such as green when indicating a value in the safe zone, yellow when the value indicates that the cushioning and support are degrading but still usable, and red when the values indicate that the cushioning and support are at a dangerous level.

Communication device 120 may communicate with a server 140 that includes a shoe type database 142 that defines characteristics of a plurality of different running shoe types from various manufacturers. Communication device 120 retrieves characteristics corresponding to running shoe 104 from database 142 and models wear of running shoe 104 to accurately determine when running shoe 104 has become worn out and thus likely to cause injury to the runner. It should be appreciated that the term "run" herein may also include jogging, walking or any other physical activity that imparts force on the body via the shoe without departing from the scope hereof. Similarly "runner" may include runners, joggers, walkers, skippers, etc.

FIG. 2 shows foot strike analyzer 100 of FIG. 1 in further example detail. Server 140 is a computer that includes at least one processor 252 and a memory 254 that may represent one or more of volatile memory (e.g., RAM) and non-volatile memory (e.g., ROM, magnetic, optical, FLASH, etc. as known in the art), each of which may be local and/or networked. Server 140 also includes software 260 that has machine readable instructions that are executed by processor 252 to implement the functionality of server 140 as described herein. In one embodiment, server 140 is implemented "in the cloud" and includes an interface (not shown) that allows accessibility via the Internet using interface 262. Memory 254 is shown storing shoe type database 142 storing a shoe type 256 in association to its corresponding shoe characteristics 258, thereby allowing characteristics 258 to be retrieved from server 140, for example by communications device 120, based upon a defined shoe type 256. Software 260 operates to generate, update, and maintain shoe type database 142 and communicate with software 136 of communication device 120 via interface 262.

Communication device 120 includes display 120 (e.g., a touch screen display), at least one processor 222, and a memory 224. Memory 224 may represent one or more of volatile memory (e.g., RAM) and non-volatile memory (e.g., ROM, magnetic, optical, FLASH, etc. as known in the art). Memory 224 is shown storing a runner profile 230, created by a runner via interaction with communication device 120, that defines certain characteristics of the runner that are pertinent to running shoe 104, including a shoe type 232 that defines a manufacturer and a model of running shoe 104. Software 136 includes machine readable instructions that are executed by processor 222 to implement functionality of communication device 120 described herein.

Communication device 120 includes an interface 226 that facilitates communication with server 140, such as via the Internet and other wired and wireless networks. In one embodiment, interface 226 implements a cellular based data communication protocol for connecting to the Internet via a cellular communication provider. In another embodiment, interface 226 implements a Wi-Fi protocol that allows communication device 120 to communicate with server 140 via a wireless network and the Internet. Software 136 retrieves, based upon shoe type 232 and via interface 226, corresponding shoe characteristics 258 from database 142. Software 136 then implements a model 234 based upon both runner profile 230 and shoe characteristics 258. Communication device 120 also includes an interface 228 that communicates with foot strike monitor 102. Interface 228 may implement a short range wireless communication protocol such as Bluetooth, Bluetooth Low-Energy, or other such protocols.

Utilizing both runner profile 230 and shoe characteristics 258 allows model 234 to be uniquely tailored to each runner and their selected running shoe 104, and thereby more accurately predict the wear on the shoe 104. Characterizing both the shoe and the runner within model 234, allows model 234 to accurately predict the change in cushioning and protection provided by the shoe over time, and thereby predict when the shoe will no longer provide sufficient cushioning and protection. For example, based upon the unique stride and history of the user, model 234 adjusts the total miles that a shoe may be worn. Model 234 also adds or subtracts miles based upon characteristics of the particular shoe. Then, model 234 uses sensor data to determine a percent increase from a baseline and/or over five consecutive sessions during which preset threshold values are crossed.

Foot strike monitor 102 includes at least one processor 202, a memory 204, at least one sensor 208, and an interface 212. Memory 206 represents one or more of volatile memory (e.g., RAM) and non-volatile memory (e.g., ROM, magnetic, optical, FLASH, etc. as known in the art), and is shown storing software 206. Sensor 208 is for example three accelerometers that measure acceleration in three orthogonal directions simultaneously. In another embodiment, sensors 208 are implemented as two orthogonal linear accelerometers and a rotational accelerometer and/or gyroscope. More or fewer accelerometers and gyroscopes may be implemented without departing from the scope hereof. Software 206 includes machine readable instructions that are executed by processor 202 to read sensor data 210 from one or more sensors 208 and stores sensor data 210 within memory 204. For example, at least part of memory 204 may form a circular buffer (or other type of memory buffer) that receives and stores sensor data 210 prior to transfer to communication device 120. Foot strike monitor 102 also includes an interface 212 that facilitates communication with communication device 120. For example, interface 212 is configured with a protocol matching that of interface 228 to enable transfer of sensor data 210 to communication device 120. As sensor data 210 is successfully transferred to communication device 120 is may be removed from memory 204.

Foot strike monitor 102 may collect sensor data 210 within memory 204 even when not in communication with communication device 120, transferring stored sensor data 210 to communication device 120 when communication is next established. In one example of operation, the runner wears running shoe 104 for a run and does not take communication device 120, wherein foot strike monitor 102 senses and records sensor data 210 during the run. After completing the run, the runner returns to proximity of communication device 120 and sensor data 210 is automatically transferred to communication device 120 for processing by software 136 using model 234.

Figure 3:
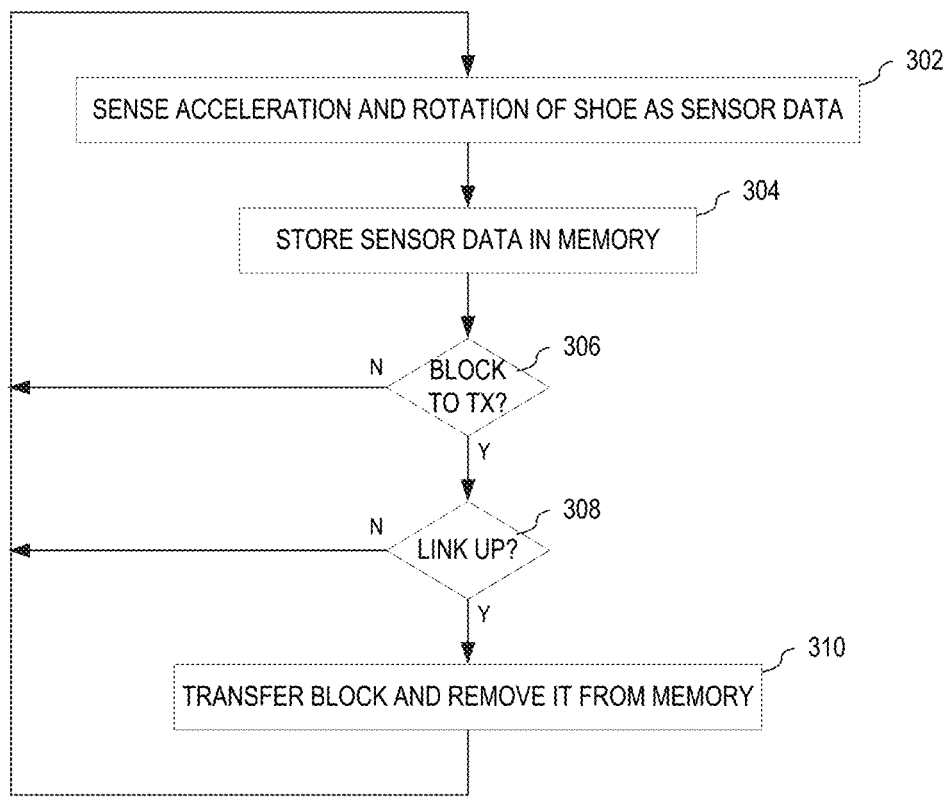
FIG. 3 is a flowchart illustrating one example method for sensing foot strikes, in an embodiment.

FIG. 3 is a flowchart illustrating one example method 300 for sensing foot strikes. Method 300 is for example implemented within software 206 of foot strike monitor 102.

In step 302, method 300 senses acceleration and rotation of the shoe as sensor data. In one example of step 302, software 206 is executed by processor 202 to read sensor data 210 from at least one sensor 208. In step 304, sensor data is stored in the memory. In one example of step 304, software 206 is executed by processor 212 to store sensor data 210 within memory 204.

Step 306 is a decision. If, in step 306, method 300 determines that a block of sensor data is ready to transmit, method 300 continues with step 308; otherwise, method 300 continues with step 302. Steps 302, 304, and 306 repeat to store sensor data 210 within memory 204.

Step 308 is a decision. If, in step 308, method 300 determines that the link to the communication device is up, method 300 continues with step 310; otherwise, method 300 continues with step 302. Steps 302, 304, 306, and 308 repeat to store sensor data 210 within memory 204 and until interface 212 and interface 228 of communication device 120 have established communication.

In step 310, method 300 transfers a block of sensor data 210 to communication device 120 and removes the block of sensor data 210 from memory 204. In one example of step 310, software 206 is executed by processor 202 to transfer sensor data 210 from memory 204 to communication device 120 via interface 212 (and corresponding interface 228 of communication device 120). Upon successful transfer and a block of sensor data 210 to communication device 120, software 206 deletes the block of sensor data 210 from memory 204.

Figure 4:
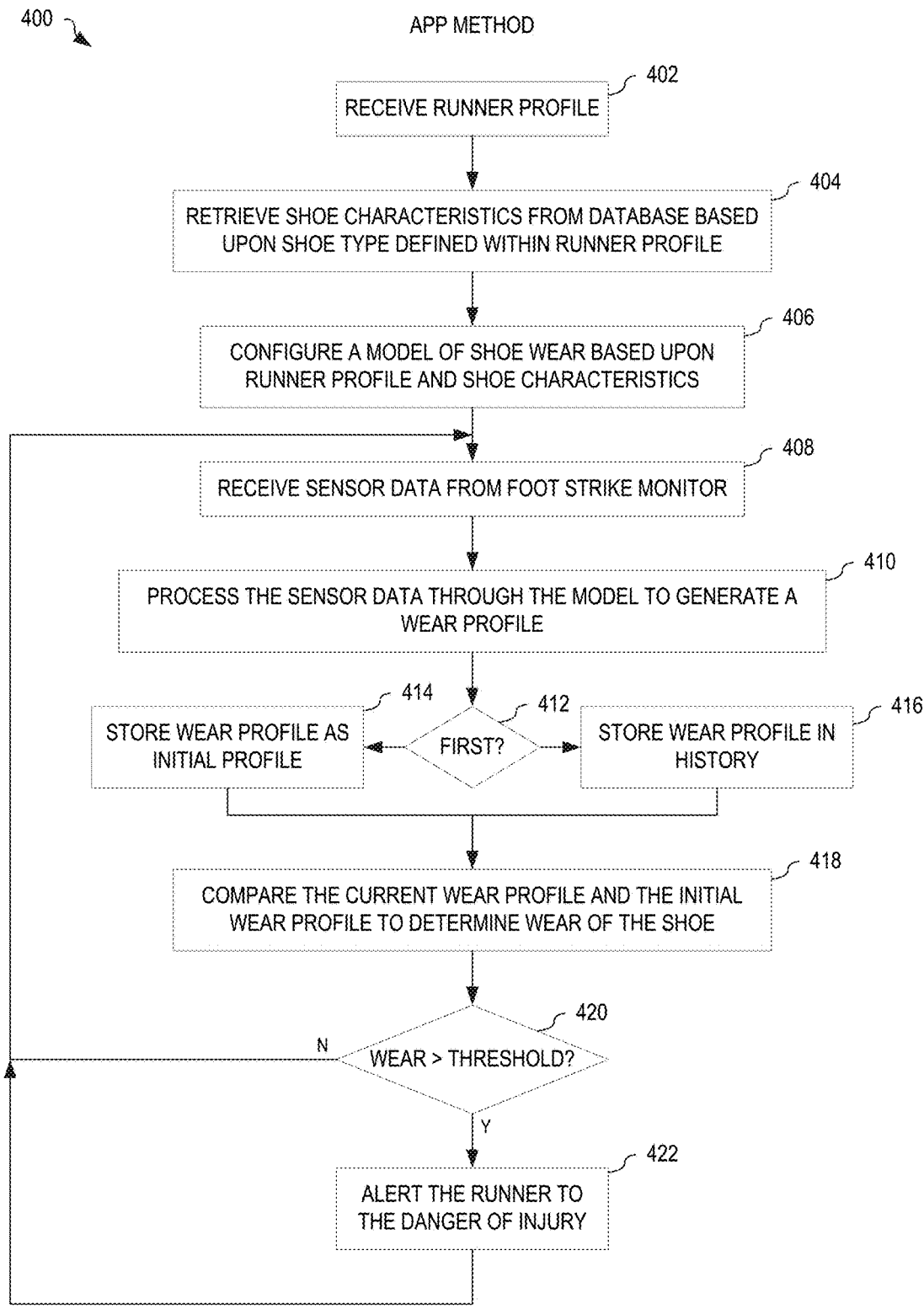
FIG. 4 is a flowchart illustrating one example method for receiving and modeling sensor data within the communication device of FIG. 1 to determine wear, and expected life, of the shoe, in an embodiment.

FIG. 4 is a flowchart illustrating one example method 400 for receiving and modeling sensor data within communication device 120 to determine wear, and expected life of, shoe 104. Method 400 is implemented in software 136 of communication device 120, for example.

In step 402, method 400 receives a runner profile. In one example of step 402, software 136 is executed by processor 222 to interact, via display 122, with a runner (e.g., the user) of communication device 120 to receive runner profile 230 that defines at least shoe type 232. In step 404, method 400 retrieves shoe characteristics from a database based upon the shoe type defined within the runner profile. In one example of step 404, software 136, executed by processor 222, sends shoe type 232 to server 140 and receives, in return, shoe characteristics 258 corresponding to the sent shoe type 232 as determined by matching, within server 140, shoe type 256 of shoe type database 142 with shoe type 232.

In step 406, method 400 configures a model of shoe wear based upon the runner profile received in step 402 and the shoe characteristics retrieved in step 404. In one example of step 406, software 136 generates model 234 based upon runner profile 230 and shoe characteristics 258. Model 234 determines a baseline/initial impact value for a new (non-worn) shoe, which is measured by the foot strike monitor 102 and delivered to the model as sensor data 210. Once the baseline for the shoe is set, model 234 determines a wear threshold and expected change in impact forces that indicates when the shoe (e.g., foam) is worn out and needs to be replaced based upon shoe type 232, runner profile 230 and shoe characteristics 246 received from the server 140.

In step 408, method 400 receives sensor data from the foot strike monitor. In one example of step 408, software 136 is executed by processor 222 to receive a block of sensor data 210 from foot strike monitor 102 via interface 228 (and interface 212 of foot strike monitor 102). In step 410, method 400 processes the sensor data through the model to generate a wear profile. In one example of step 410, software 136 processes sensor data 210 through model 234 to generate modeled data 236 based upon runner profile 230 and shoe characteristics 258.

Step 412 is a decision. If, in step 412, method 400 determines that the received sensor data is the first received for running shoe 104, method 400 continues with step 414; otherwise, method 400 continues with step 416.

In step 414, method 400 stores the wear profile as an initial wear profile. In one example of step 414, software 136 is executed by processor 222 to store modeled data 236 as initial wear profile 238 for running shoe 104. Method 400 then continues with step 418. In step 416, method 400 stores wear profile of step 410 in wear history 439. Wear history 439 thereby forms a history profile of wear on running shoe 104 within memory 224. In one embodiment, software 136 may also send modeled data 236 to server 140 for further processing. For example, server 140 may utilize modeled data 236 received from a plurality of runners to more accurately determine how shoe 104 wears, and thereby generate and/or modify shoe characteristics 258 accordingly. Method 400 continues with step 418.

In step 418, method 400 compares the current wear profile and the initial wear profile. In one example of step 418, software 136 is executed by processor 222 to compare modeled data 236 against initial wear profile 238 to determine a wear factor 242 of running shoe 104. In one embodiment, wear factor 242 is a value indicating measured wear on running shoe 104 based upon model 234.

Step 420 is a decision. If, in step 420, method 400 determines that the wear factor determined in step 418 is greater than the wear threshold (determined in step 406), method 400 continues with step 422; otherwise, method 400 continues with step 408. Steps 408 through 420 repeat for each received block of sensor data 210.

In step 422, method 400 alerts the runner to the danger of injury from continued use of the running shoe. In one example of step 422, software 136 generates a warning message on display 122 to indicate that running shoe 104 is worn out and may cause injury. Method 400 then continues with step 408 to continue processing received sensor data through model 234.

Figure 5A:
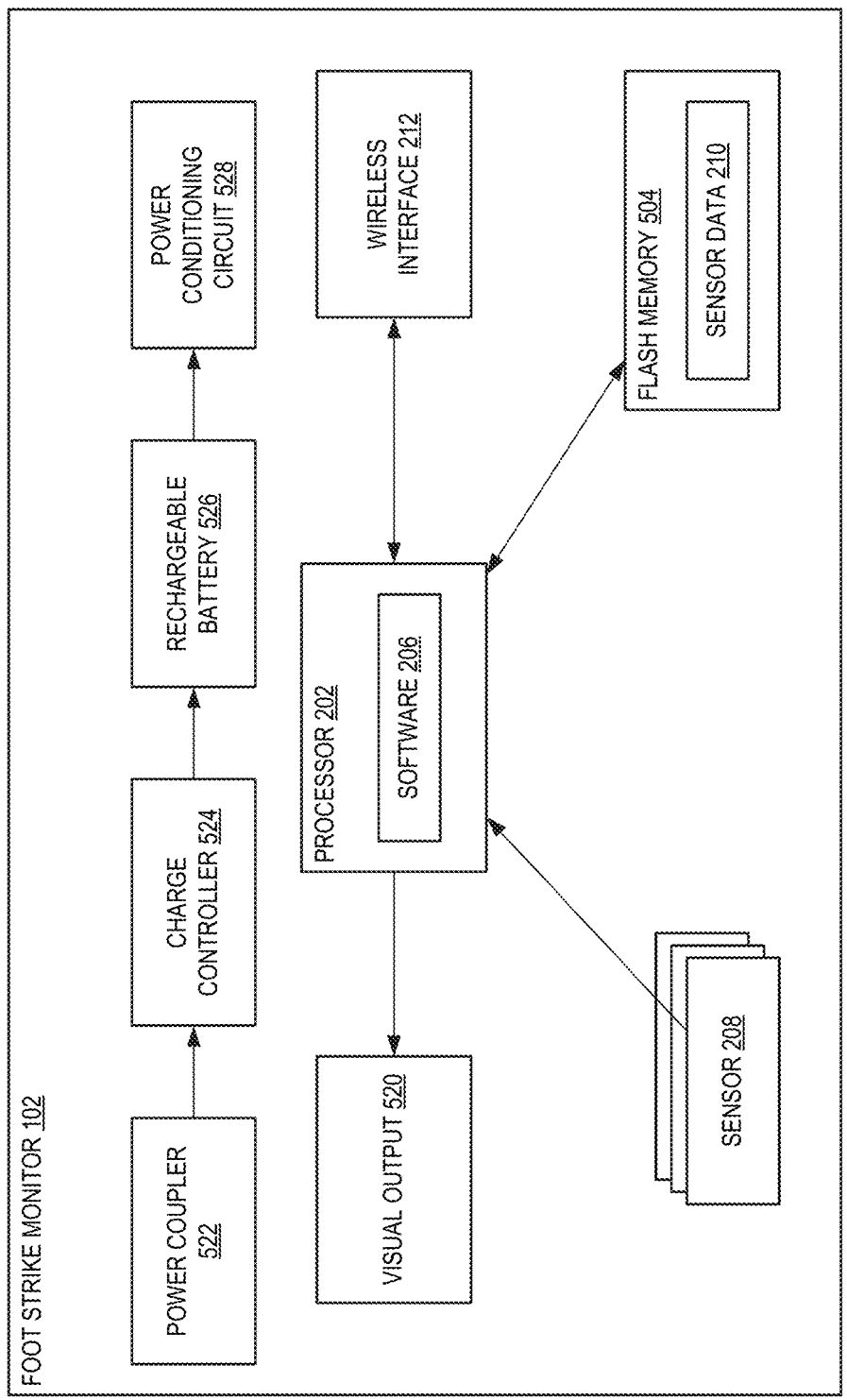
FIG. 5A is a block diagram illustrating example detail of the foot strike monitor of FIGS. 1 and 2 in an embodiment.
Figure 5B:
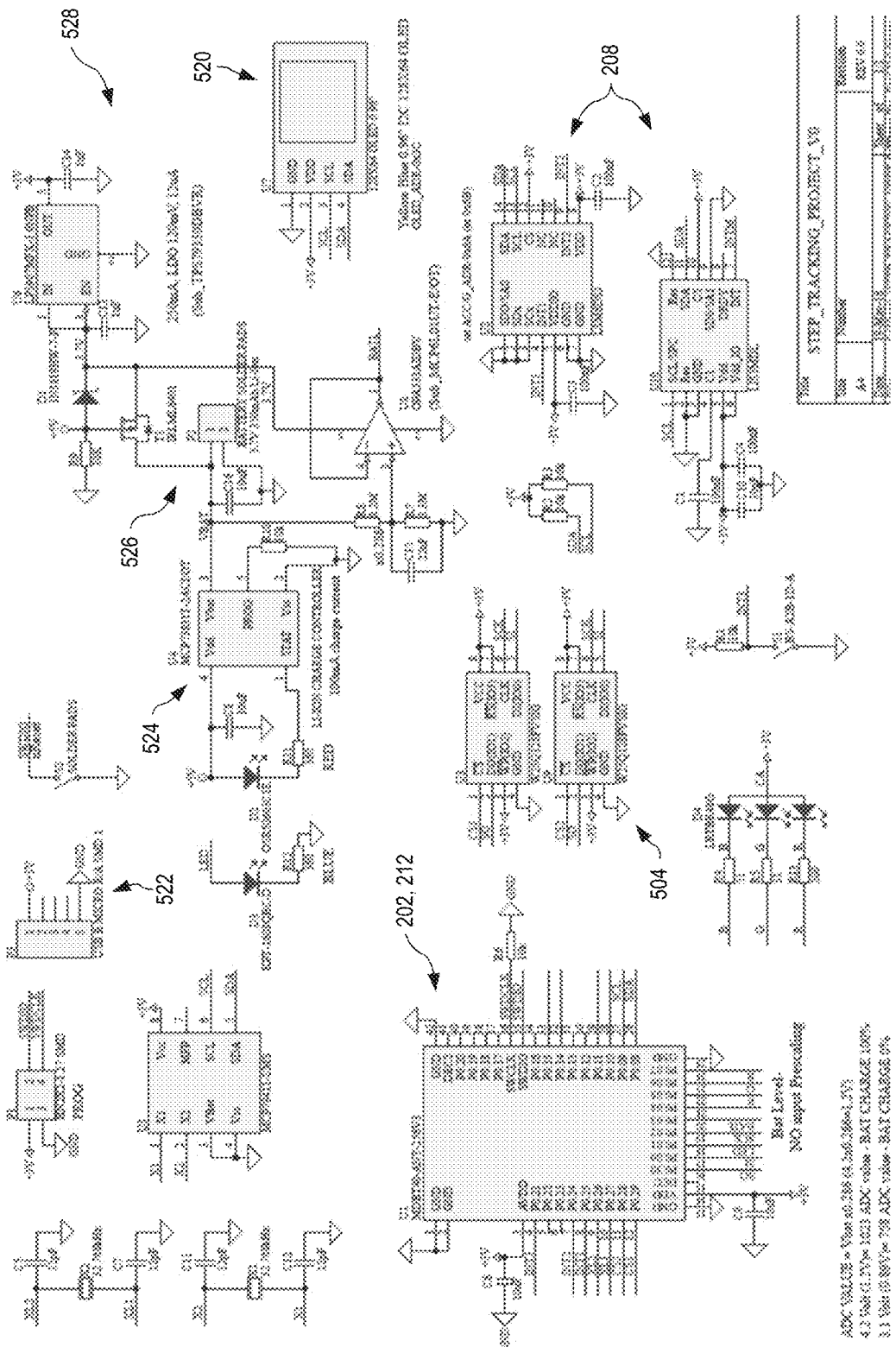
FIG. 5B is a schematic diagram illustrating example circuitry for implementing the foot strike monitor of FIG. 5A, in an embodiment.

FIG. 5A is a block diagram illustrating example detail of foot strike monitor 102 of FIGS. 1 and 2 in an embodiment. FIG. 5B is a schematic diagram illustrating example circuitry for implementing foot strike monitor 102 of FIG. 5A. FIGS. 5A and 5B are best viewed together with the following description.

Foot strike monitor 102 includes a flash memory 504 for storing sensor data 210. Software 206 is shown within processor 202, which may represent a microcontroller that includes RAM, ROM, and FLASH memory, as known in the art. Flash memory 504 may be communicatively coupled to processor 202 using an I2C (two wire) bus. Processor 202 and wireless interface 212 are implemented within a single integrated circuit, and multiple sensors 208 are implemented within a single integrated circuit. Optionally, foot strike monitor 102 includes an visual output 520, which may be implemented as an OLED matrix display that connects to processor 202 using the I2C bus. Visual output 520 allows the runner to utilize foot strike monitor 102 without using communication device 120 and app 136. For example, visual output 520 may be configured to show one or more of miles left 1012, impact 1004, and pronation 1008, or any other parameter that is displayed by app 136.

Foot strike monitor 102 also includes a power coupler 522 that received external power (e.g., a wired connection or an inductive coupling), a charge controller 524, a rechargeable battery 526, and power conditioning circuit 528. Power coupler 522 and charge controller 524 cooperate to charge rechargeable battery 526 when power is provided to power coupler 522. Rechargeable battery 526 and power conditioning circuit 528 cooperate to provide power to processor 202, wireless interface 212, sensors 208, flash memory 504, and visual output 520 (if included). In one embodiment, sensors 208 are implemented by an STMicroelectronics LSM6DSLTR iNEMO inertial module that includes a 3D accelerometer and a 3D gyroscope.

As appreciated, other integrated circuits and components may be used to implement foot strike monitor 102 without departing from the scope hereof.

Figure 6:
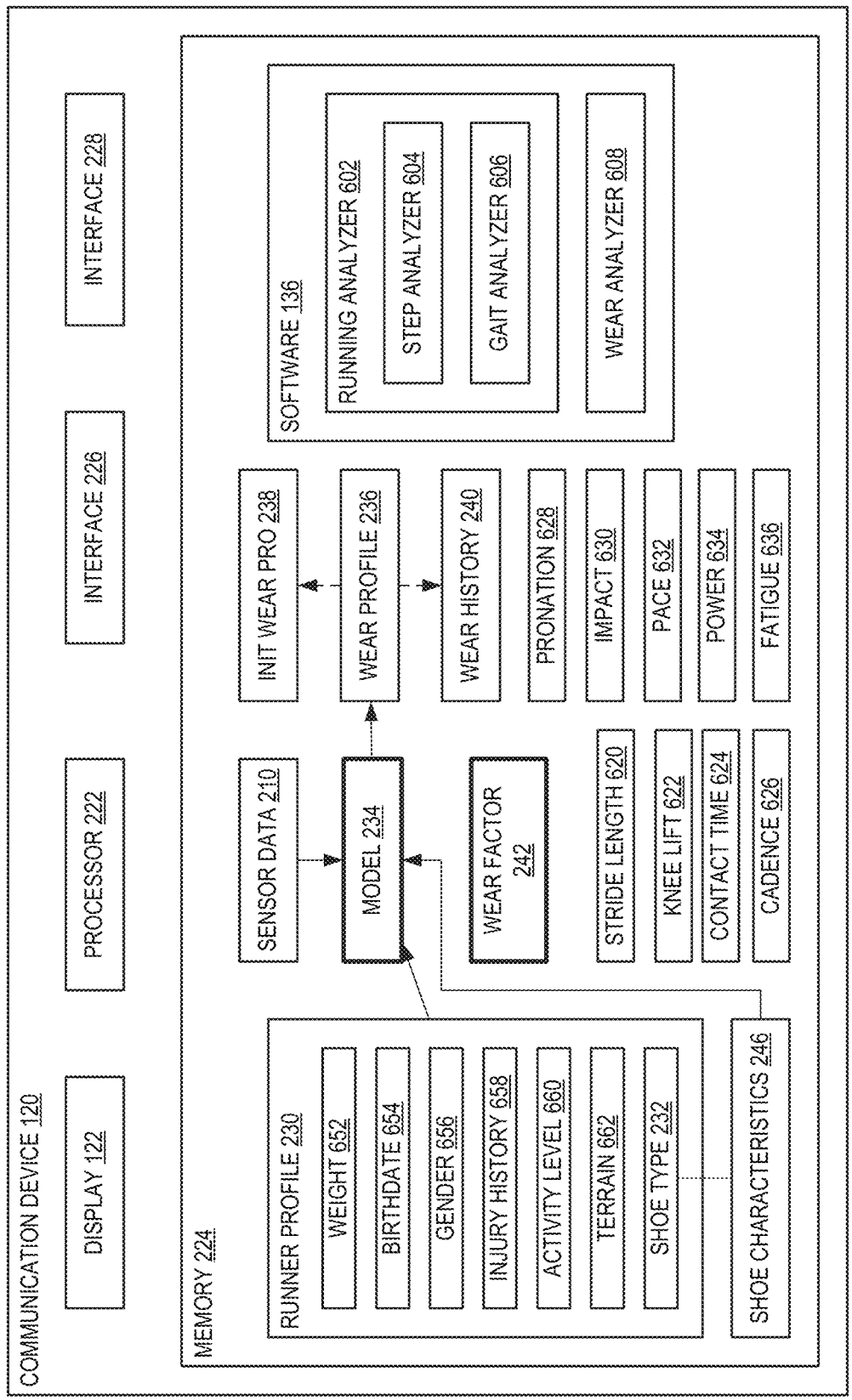
FIG. 6 is a block diagram illustrating further example detail of the communication device of FIG. 1, in an embodiment.
Figure 7:
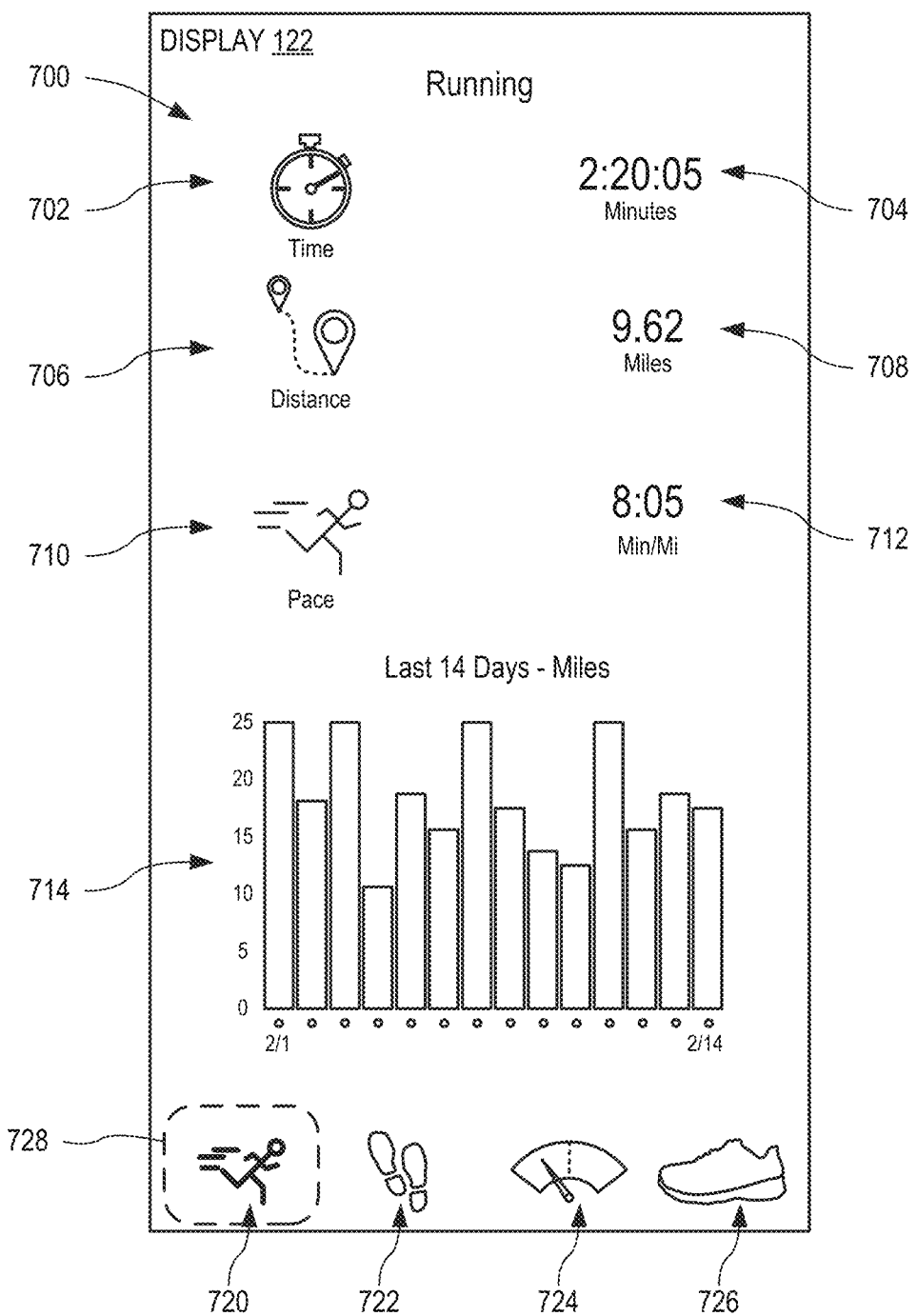
FIGS. 7, 8, 9, and 10 show example screens generated by the running analyzer of FIG. 6, in embodiments.
Figure 8:
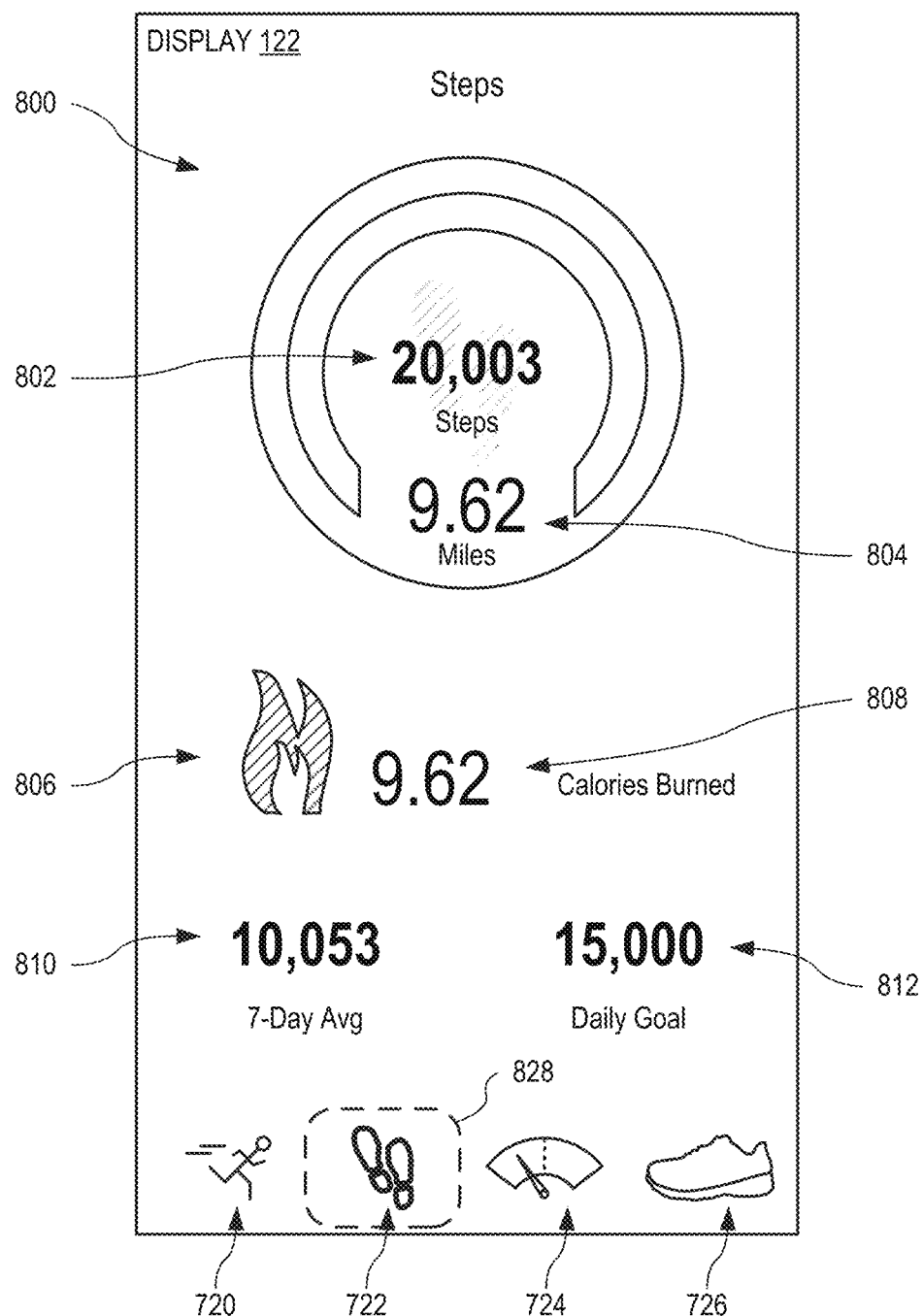
Figure 9:
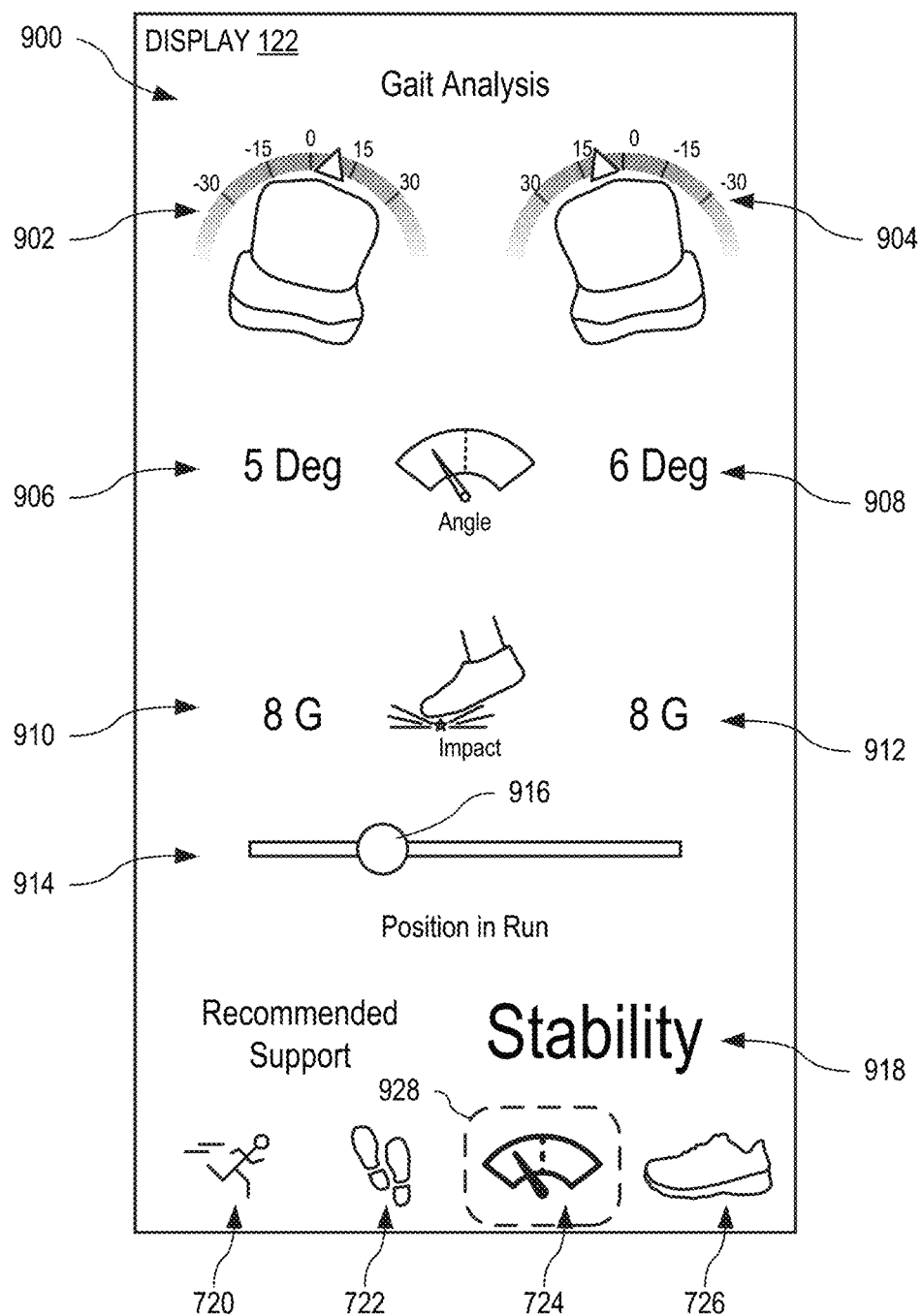
Figure 10:
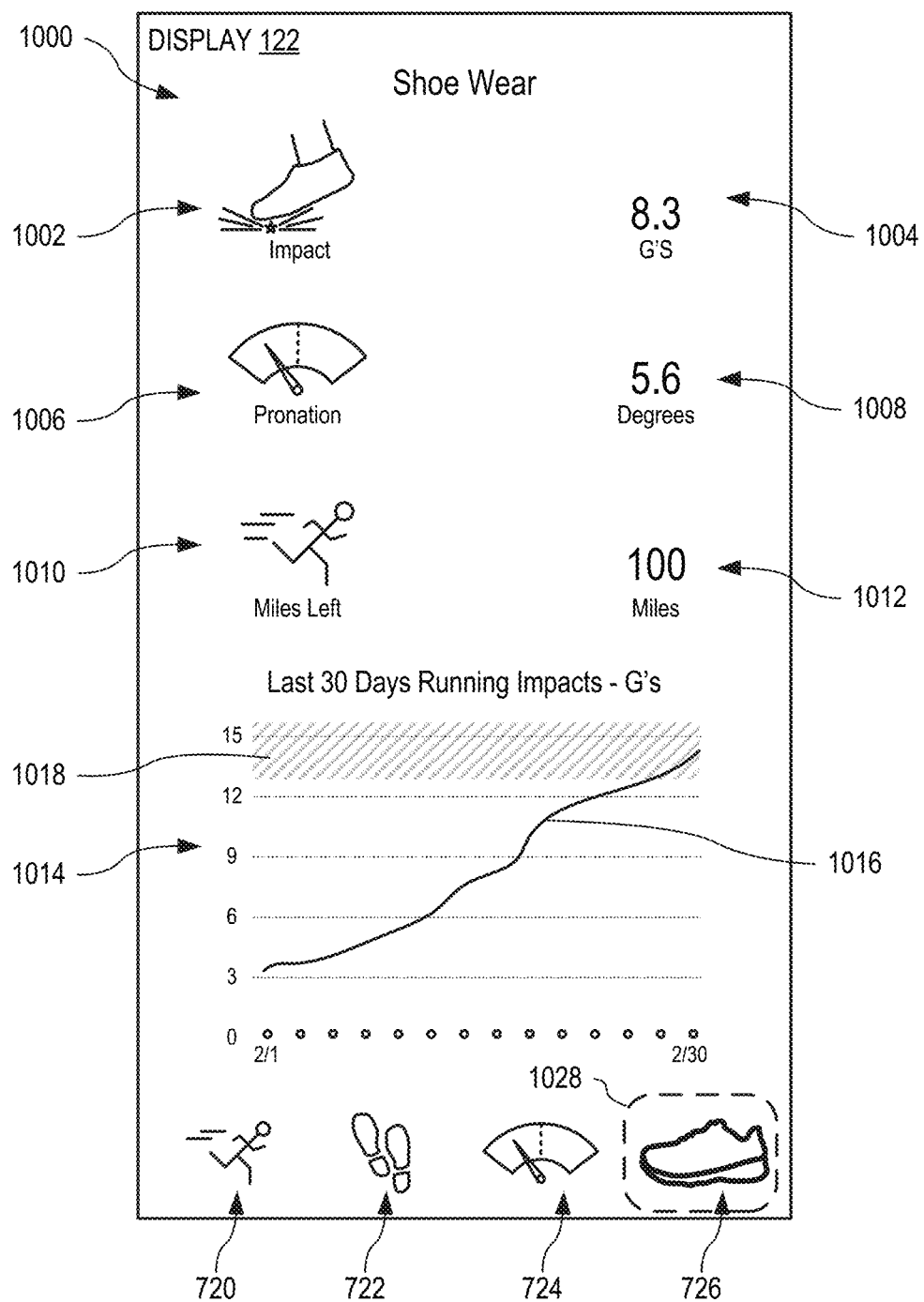

FIG. 6 is a block diagram illustrating further example detail of communication device 120 of FIG. 1. Software 136 includes a running analyzer 602, a step analyzer 604, a gait analyzer 606, and a wear analyzer 608. Further to shoe type 232, runner profile 230 may also include details of the runner. For example, the runner may define one or more of a weight 652, a birthdate 654, a gender 656, an injury history 658, an activity level 660, and a default terrain 662. Weight 652 is used within model 234 to determine the impact felt when running. Age may be determined from birthdate 654 and used within model 234 to estimate bone density of the runner and a healing rate, which changes as the runner ages. Gender 656 may also be used to estimate the bone density of the runner, since bone density of women and men differ and may be adjusted within model 234. Injury history 658 may be used within model 234 to determine whether the runner is more or less susceptible to injury, thereby determining the level of cushioning and support needed from the shoe. Terrain 662 defines the type of terrain that the runner expects to run on and affects the time that a shoe will last as well as the impact felt through the shoes. For example, running on dirt reduces results in a lower impact on the body as compared to running on concrete, which has a higher impact level. All of these parameters may be utilized within model 234 to either increase or decrease the predicted wear out of shoe 104.

FIGS. 7, 8, 9, and 10 show example screens 700, 800, 900, and 1000, respectively, generated by running analyzer 602 of FIG. 6. FIGS. 6 through 10 are best viewed together with the following description.

Four icons 720, 722, 724, and 726 are displayed at the bottom of each screen 700, 800, 900, and 1000, and may be selected by the runner to display the corresponding screen 700, 800, 900, and 1000, respectively. As shown, when each screen 700, 800, 900, and 1000 is displayed, the corresponding icon 720, 722, 724, and 726, is highlighted, as indicated by dashed outlines 728, 828, 928, and 1028, respectively.

As shown on screen 700, running analyzer 602 allows the runner to track a time and a distance for each run. Further, running analyzer 602 processes at least part of sensor data 210 to determine one or more of a stride length 620, knee lift 622, ground contact time 624, cadence 626, pronation 628, impact 630, pace 632, power 634, and fatigue point 636. This information provides the runner with immediate coaching and feedback on their running performance, and by analyzing sensor data 210 recorded during the run, running analyzer 604 illustrates changes in the running performance. For example, stride length 620, knee lift 622, ground contact time 624, cadence 626, pronation 628, impact 630, pace 632, power 634 may change during the run and fatigue point 636 may be determined.

Running analyzer 602 may also send at least part of sensor data 210, or results from processing sensor data 210, to server 140 for further analysis. For example, server 140 may implement a website that allows more detailed analysis of the run, and comparison of that run to previous runs and run made by other runners. The web site may also generate recommendations for improving the runner's performance (e.g., bettering stride length and running efficiency). The website may also provide exercises and coaching to help the runner eliminate the changes identified by running analyzer 602 during the run, and thereby further improve the runner's performance and help prevent injuries.

Screen 700 shows exemplary output from running analyzer 602, including a duration of the run, indicated by icon 702 and time value 704, a distance of the run, indicated by icon 706 and distance value 708, and a pace of the run, indicated by icon 710 and pace value 712. Screen 700 also shows a graph 714 illustrating the number of miles run over the last fourteen days.

Screen 800 shows a step count 802, a distance value 804, and a calories burned value 808 indicated with an icon 806, for a current run, as generated by a step analyzer 604 portion of running analyzer 602. Screen 800 also shows a seven-day average step count 810 and a configurable daily goal step count value 812.

Screen 900 shows a left shoe pronation graphic 902 and a left shoe pronation value 906, a right shoe pronation graphic 904 and a right shoe pronation value 908, as generated by a gait analyzer 606 portion of running analyzer 602. Screen 900 also displays an impact force value 910, 912, for each shoe. Left and right values are determined and displayed when the runner is using two foot strike monitors 102, one on each of the left and right running shoes. Otherwise, a single value may be determined and displayed for each of pronation and impact force.

A slider 914 allows the runner to move a run position control 916 to display pronation and impact force for any part of the selected or current run. That, the runner may evaluate how their gait changed over the duration of the run.

Gait analyzer 606 may also generate a recommendation for shoe support type, as indicated by shoe support type display 918, based upon processing of sensor data 210. For example, the recommended shoe support type may be one of neutral, stability, motion control, and minimalist, depending upon the pronation and strike force measured over a run.

Previously, gait analysis was determined from video captured of a runner's foot while running. A person then evaluated the video to determine pronation, however, the video provided no indication of forces felt by the runner. System 100 facilitates capture movement of the runner's foot and allows both pronation and force to be determined.

The determined pronation may also be used within model 234 to determine wear on shoe 104. For example, as shoe 104 wears, the stiffer foam or stability aspect in shoes remains sturdy but the soft cushioning foam wears down. This causes the runner's foot to rotate within the shoe. Further, where shoe 104 is not suited to the runner (i.e., the runner is using the wrong type or size of shoe), their foot is more likely to pronate and may cause injury. In one embodiment, model 234 is configured with a threshold corresponding to the degree of pronation, that triggers an alert to warn the runner of possible injury. For example, where shoe 104 is not correct for the runner, communication device 120 may immediately alert the runner to risk of injury—indicating wrong shoes as a cause. Where pronation increases as the shoe wears, this pronation is factored into the determination of the remaining life of the shoe.

Screen 1000 is generated by wear analyzer 608 based upon modeled data 236, wear history 240, and wear factor 242 generated by model 234 and impact forces generated by gait analyzer 606. For example, wear analyzer 608 operates model 234 to generate wear factor 242 as described above, to display an impact icon 1002 with a corresponding average impact force value 1004, a pronation icon 1006 and a corresponding average pronation value 1008, and a remaining life icon 1010 with a corresponding estimated distance remaining value 1012 for running shoe 104. Estimated distance remaining value 1012 is determined from wear factor 242 and wear history 240.

Screen 1000 also displays an impact graph 1014 with a line 1016 representing impact force measures for running shoe 104 over the last thirsty days. A danger area 1018 represents an impact force level where protection provided by shoe 104 is insufficient to ensure that injury will not occur, and thus indicates when shoe 104 is worn out.

Figure 11:
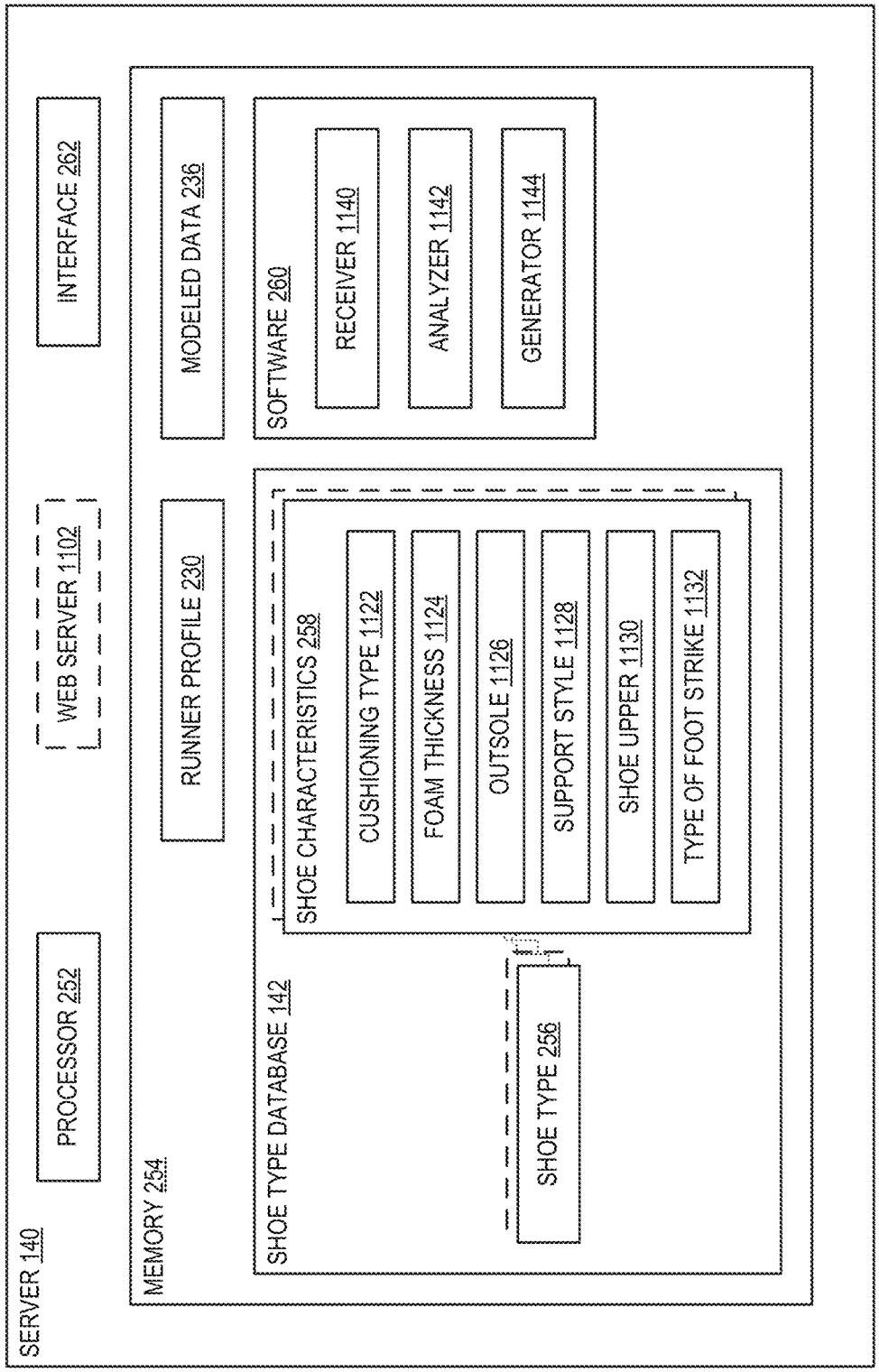
FIG. 11 shows further example detail of the server and the shoe type database of FIGS. 1 and 2, in embodiments.

FIG. 11 shows server 140 and shoe type database 142 of FIGS. 1 and 2 in further example detail. Shoe characteristics 258 may include one or more of a cushioning type 1122, a foam thickness 1124, an outsole 1126, a support style 1128, a shoe upper 1130, and a type of foot strike 1132. Cushioning type 1122 may be selected from the group including EVA Foam, Gel, TPU, and plastic. Support style 1128 may be selected from the group including: neutral, stability, motion control, and minimalist. Each of these characteristics may be used within model 234 of communication device 120 to characterize sensor data 210 based upon the defined characteristics of both the runner (e.g., runner profile 230) and shoe characteristics 258. Cushioning type 1122 is important because each cushioning type breaks down at a different rate. Foam thickness 1124 defines how much surface area and how fast the foam pockets may break down (wear). Support style 1128 defines which of many different densities of foam are used to provide support in the shoe. Foot strike 1132 defines where (relative to the foot) the runner strikes hardest, which is important as the thickness of the cushioning is different at the front of the shoe as compared to the rear of the shoe. Outsole 1126 and shoe upper 1130 define the shock absorption and wear out time for the shoe.

Software 260 includes a receiver 1140 that cooperates with interface 262 to receive modeled data 236 from communication device 120. Software 260 also includes an analyzer 1142 for analyzing modeled data 236 from a plurality of runners and a generator 1144 for generating and updating shoe characteristics 258 accordingly. Analyzer 1142 may also analyze modeled data 236 for many different shoe types to determine a particular shoe type 256 that is suitable for a runner based upon a received runner profile 230. For example, runner profile 230 and modeled data 236 may be analyzed and compared to those of other runners to determine a type of shoe that best suits the running style and characteristics detected by foot strike monitor 102.

Server 140 collects modeled data 236 from many runners using many different shoe types 256 over time and analyzer 1142 uses this data to improve model 234 and wear prediction and accuracy of shoe characteristics 246. That is, algorithms within analyzer 1142 and software 136 are learning based and becomes more accurate as more sensor data 210 is collected.

Further, shoe characteristics 246 and modeled data 236 may be provided to other entities (e.g., consumer reports and/or wear testers) as a way of rating of shoes in for impact reduction. This large volume of data may provide a more scientific review of a running shoe brand and model that may be used as a standard for the running shoe market.

System 100 may also be used to provide recommendation to a customer in a shoe store. For example, where a customer enters a store (e.g., a running specialty store) looking to buy new running shoes, a salesman may recommend that the customer have a gait analysis in order to identify the right type of support required from the new running shoe. Accordingly, one foot strike monitor 102 is attached to each of the new running shoes, and the customer runs (e.g., on a treadmill, on a level track, or on a level concrete strip) while a communication device 120 of the salesman receives and models sensor data 210 from both foot strike monitors 102. For example, the customer may run for between one and five minutes. Once the running is complete, the salesman selects screen 900 to show left shoe pronation graphic 902, left shoe pronation value 906, right shoe pronation graphic 904, and a right shoe pronation value 908, impact force values 910, 912 for each shoe, and show support type display 918 that indicates a recommendation for a particular shoe support. The salesman may utilize slider 914 to display pronation and impact force information for any part of the customer's run. Optionally, modeled data 236 corresponding to the customer's run may be sent to server 140 for further analysis and comparison by analyzer 1142.

Figure 12:
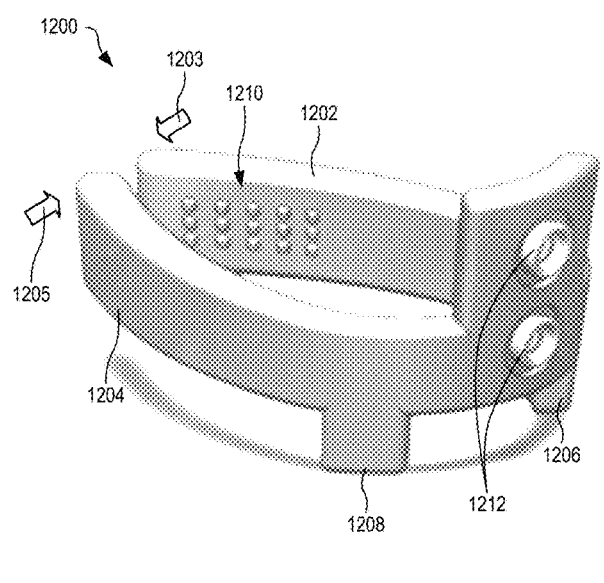
FIG. 12 shows one example temporary attachment device for attaching the foot strike monitor of FIG. 1 to the shoe, in an embodiment.
Figure 13:
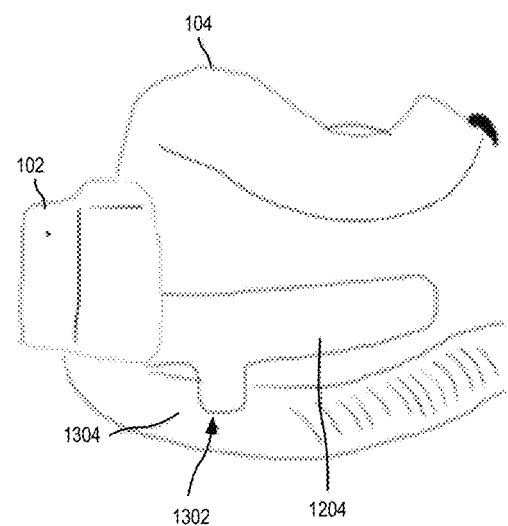
FIG. 13 shows the temporary attachment device of FIG. 12 attached to the shoe.

FIG. 12 shows one example temporary attachment device 1200 for attaching foot strike monitor 102 to shoe 104. FIG. 13 shows temporary attachment device 1200 of FIG. 12 attached to shoe 104. FIGS. 12 and 13 are best viewed together with the following description.

Temporary attachment device 1200 is a horseshoe shaped clip that has two arms 1202 and 1204 that provide an inward clamping force, indicated by arrows 1203 and 1205, inward around the heel of shoe 104 when positioned thereon. The clamping force is created by properties of the materials used for arms 1202, 1204, such as spring form steel and/or polycarbonate plastic. Inner surfaces 1210 of arms 1202, 1204 may be textured (e.g., protrusions) or have a gripping material (e.g., a tacky rubber or silicon material) that helps retains temporary attachment device 1200 to the heel of shoe 104. Temporary attachment device 1200 also has two tabs 1206, 1208, that protrude down at either side of the foot strike monitor 102 (when attached) to contact or protrude into foam of the sole of shoe 104 to minimize bounce of foot strike analyzer 102 and to improve accuracy and reliability of sensors 208 (e.g., the accelerometers and/or gyroscopes) to forces felt by a runner using the shoe. Temporary attachment device 1200 is configured (e.g., sized and shaped) to follow the contour of shoe 104 where the mesh upper and the foam cushioning meet, thereby taking advantage of the small lip on the foam/mesh interface for support. Foot strike monitor 102 attaches to temporary attachment device 1200 using attachment clips 1212 for example, o be positioned as high as possible and not hang down too low on the foam of the shoe. When coupled with temporary attachment device 1200 and positioned on shoe 104, the foot strike monitor is also positioned to be perpendicular to the ground to provide the best data. Foot strike monitor 102 may be retained within temporary attachment device 1200 by tabs positioned on three sides of the sensor and is built to remain attached to the clip.

Figure 14:
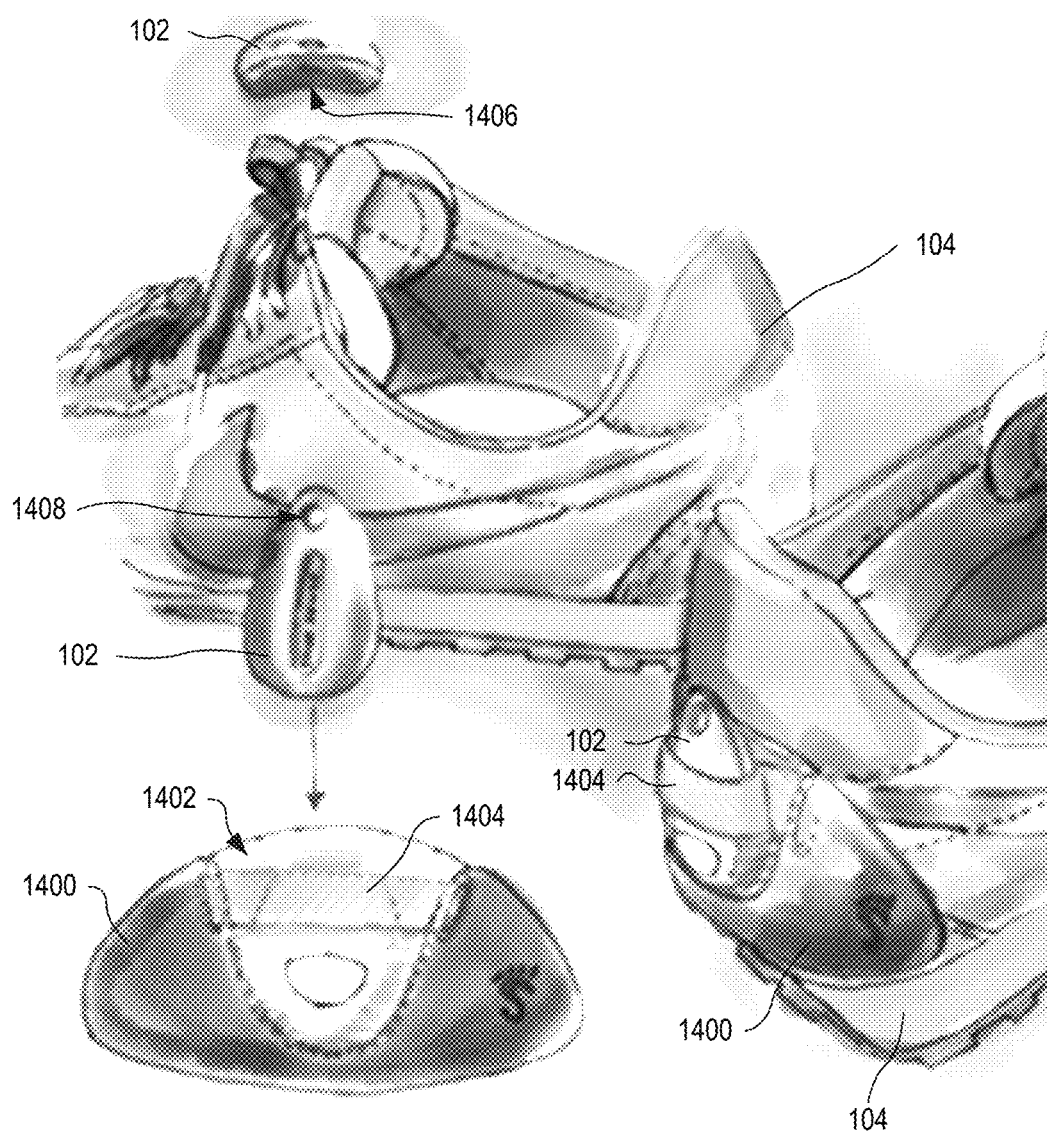
FIG. 14 shows one example permanent attachment device for attaching the foot strike monitor of FIG. 1 to the shoe, in an embodiment.

FIG. 14 shows one example permanent attachment device 1400 for attaching foot strike monitor 102 to shoe 104. Permanent attachment device 1400 may include a permanent type adhesive that bonds to the rear of shoe 104 and has a pocket for releasably receiving foot strike monitor 102.

In one embodiment, permanent attachment device 1400 is a fabric material with a pliable mesh material forming a pouch 1402 and that permanently attaches to shoe 104 via a fabric adhesive, for example. Permanent attachment device 1400 has a concave shaped back material that matches the curvature of the back of shoe 104 and may have an overall curved ovoid-like shape to prevent ingress of dirt and water. Foot strike monitor 102 sits in pouch 1402, which stretches to allow the sensor to be inserted and contracts to retain the sensor within the pouch. Permanent attachment device 1400 may include an elastic band 1404 across the top of the pouch to further prevent foot strike monitor 102 from being pushed out of the pouch. Foot strike monitor 102 may also be tapered at the top and bottom to help retain it within the pouch when there is an impact from below or above. Pouch 1402 and the backing material are stitched together and the stitch pattern is tear drop shaped (e.g., tighter at the top that the bottom) to retain the sensor in the same place during impact while the user is walking or running.

Foot strike monitor 102 may also be configured with a curved (concave) back 1406 that conforms to the shape (both the horizontal and vertical curvature) of the back of shoe 104. The outside contour of foot strike monitor 102 may be rain drop shaped allowing it to be retained in place within pouch 1402 of permanent attachment device 1400. The front/top of the foot strike monitor 102 case is tapered on the top and bottom to help avoid contact by the user when removing the shoe (e.g., by stepping on the back tab of the shoe). The bottom surface of the foot strike monitor 102 is contoured to distribute and deflect any impact from bellow such as from stairs and rocks when running. Pouch 1402 is able to withstand high impact due to flexibility of the mesh and the smooth external contours of foot strike monitor 102. To remove foot strike monitor 102 from pouch 1402 of permanent attachment device 1400, foot strike monitor 102 may have a hole 1408 in the top of the case to receive a shoelace that may be pulled vertically to remove the sensor from pouch 1402.

As illustrated in FIGS. 13 and 14, foot strike monitor 102 is preferably attached to the heel of shoe 104, since this allows more consistent sensor data 210 to be collected for each run. This heel placement also allows foot strike monitor 102 to monitor the rotation of the foot (pronation/supination) since it is vertically attached to the center of the heel. When positioned on laces of a shoe, clean and accurate data cannot be easily and consistently captured due to variability in tightness of the laces and variability in positioning of the sensor. Optimally, foot strike monitor 102 maybe built into the shoe—either in the foam or into the upper part, and preferably near the heel.

Figures 15, 16:
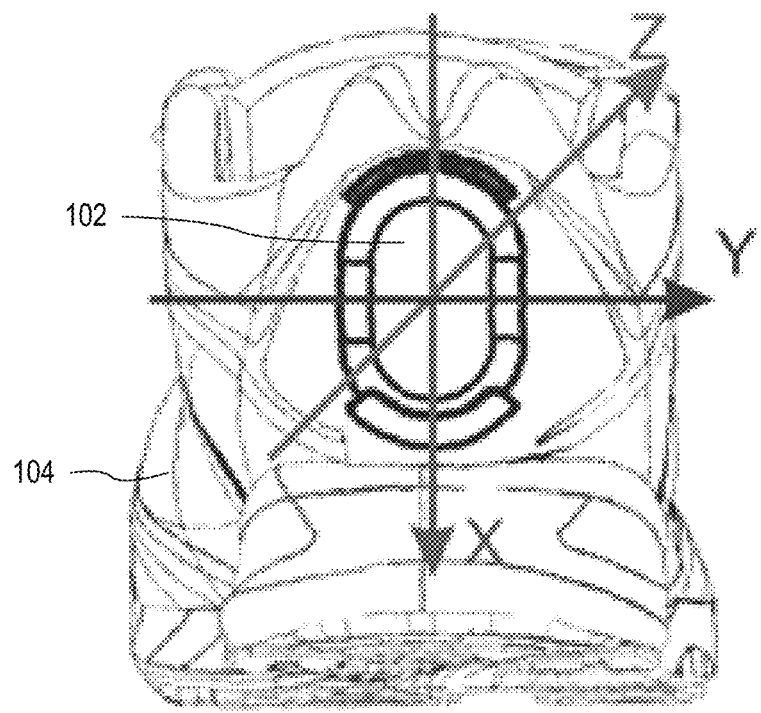
FIG. 15 shows example orientation of X, Y and Z axes used by the foot strike monitor of FIG. 1 when positioned at the rear of the shoe, in an embodiment.
FIG. 16 shows the model of FIG. 2 including a foot strike detection algorithm, a max impact force algorithm, and a pronation excursion angle algorithm, in an embodiment.

FIG. 15 shows example orientation of X, Y and Z axes used by foot strike monitor 102 when positioned at the rear of shoe 104. Sensors 208 are thus positioned to measure acceleration and rotation relative to these X, Y, and Z axes. The X axis is vertically downwards through shoe 104, the Y axis is horizontally across shoes 104, and the Z axis is horizontally along shoe 104.

FIG. 16 shows model 234 of FIG. 2 including a foot strike detection algorithm 1602, a max impact force algorithm 1604, and a pronation excursion angle algorithm 1606. Foot strike detection algorithm 1602 uses sensors data 210 from the Gyroscope Y axis (referred to as GyrY) and data from the Gyroscope Z axis (referred to as GyrZ) to detect the foot strike.

Figure 17:
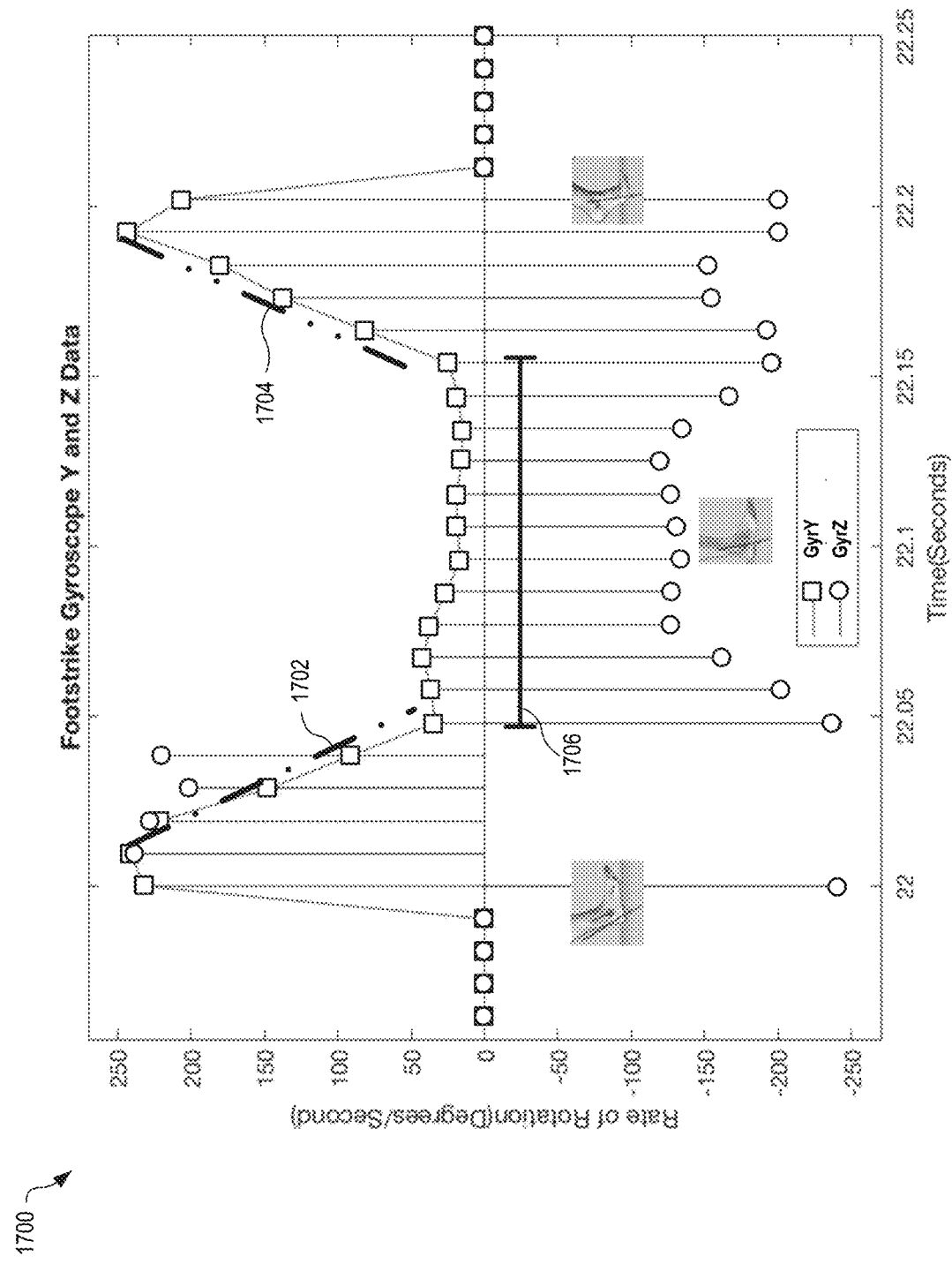
FIG. 17 is a graph illustrating example sensor data for GyrY and GyrZ during contact of the foot with the ground, as used by the foot strike detection algorithm of FIG. 16.

FIG. 17 is a graph 1700 illustrating example sensor data 210 for GyrY and GyrZ during contact of the foot with the ground, as used by foot strike detection algorithm 1602 of FIG. 16.

The gyroscope (one of sensors 208) oriented about the y-axis (see FIG. 15) collects data indicative of foot rotation from when the foot hits the ground to when the toe lifts off the ground. This enables model 234 to recognize a step accurately by pairing the impact (Ax of graph 2500, FIG. 25)

with the rotation (GyrY). For example, model 234 determines the foot hitting the ground, rotation from positive towards zero degrees as indicated by line 1702, and rotation about the z-axis (pronation and or supination) that occurs once the foot hits the ground. In the example of FIG. 17, multiple data points show a consistent rate of rotation that may be used in the model 234. The data also indicates an angle that the ankle has rotated in or out through numerically integrating the rate of rotation over the time (period 1706 of about 100 ms) the foot is rotating in or out before there is toe off as indicated by the slope of line 1704.

Figure 18:
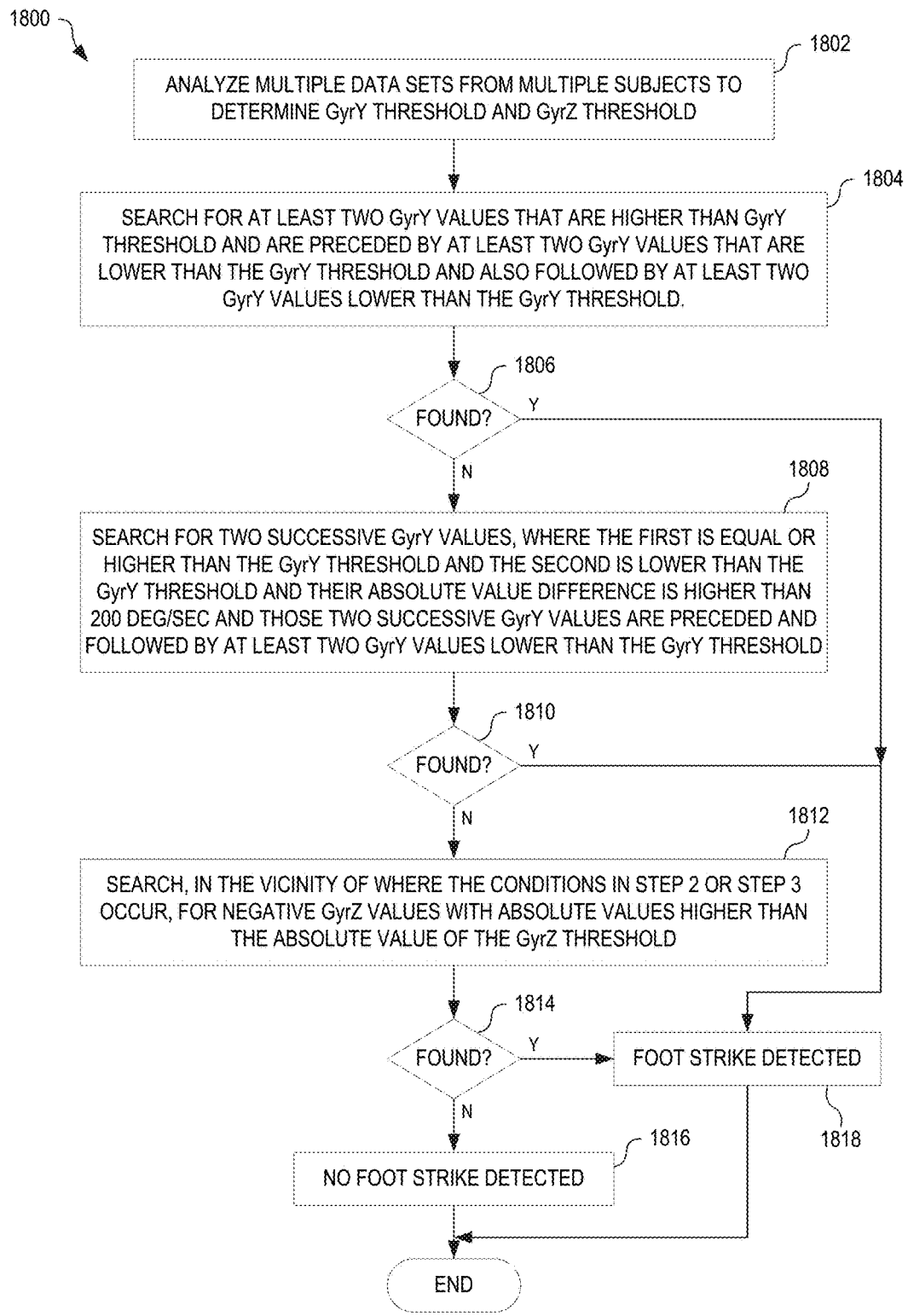
FIG. 18 is a flowchart illustrating one example method for foot strike detection, in an embodiment.

FIG. 18 is a flowchart illustrating one example method 1800 for foot strike detection. Method 1800 is implemented within foot strike detection algorithm 1602 of FIG. 16 for example.

In step 1802, method 1800 analyzes multiple data sets from multiple subjects to determine GyrY threshold and GyrZ threshold. In one embodiment, step 1802 is implemented in part within software 260 of server 140, FIG. 2, wherein server 140 collects sensor data 210 from multiple foot strike monitors 102, processes the sensor data to determine GyrY threshold and GyrZ threshold, and then communication device 120 retrieves GyrY threshold and GyrZ threshold from server 140.

Figure 21A:
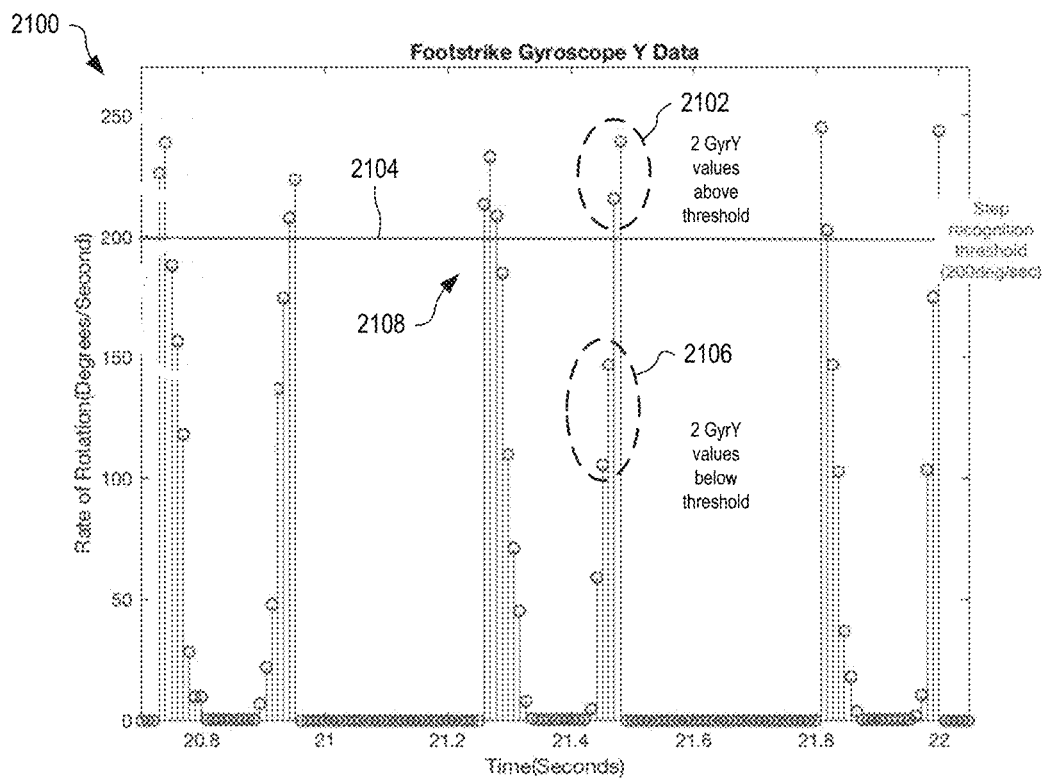
FIG. 21A is a graph showing example sensor data for GyrY during contact of the foot with the ground.

In step 1804, method 1800 searches for at least two GyrY values that are higher than the GyrY threshold and are preceded by at least two GyrY values that are lower than the GyrY threshold and also followed by at least two GyrY values lower than the GyrY threshold. FIG. 21A is a graph 2100 showing example sensor data 210 for GyrY during contact of the foot with the ground, illustrating two GyrY values 2102 above GyrY threshold 2104 that are preceded by two GyrY values 2106 that are lower than GyrY threshold 2104.

Step 1806 is a decision. If, in step 1806, method 1800 determines that the conditions of step 1804 were found, method 1800 continues with step 1818; otherwise, method 1800 continues with step 1808.

In step 1808, method 1800 searches for two successive GyrY values, where the first is equal or higher than the GyrY Threshold and the second is lower than the GyrY Threshold and their absolute value difference is higher than 200 deg/sec and those two successive GyrY values are preceded and followed by at least two GyrY values lower than the GyrY threshold. See for example, points 2108 in FIG. 21A.

Step 1810 is a decision. If, in step 1810, method 1800 determines that the conditions of step 1808 were found, method 1800 continues with step 1818; otherwise, method 1800 continues with step 1812.

Figure 21B:
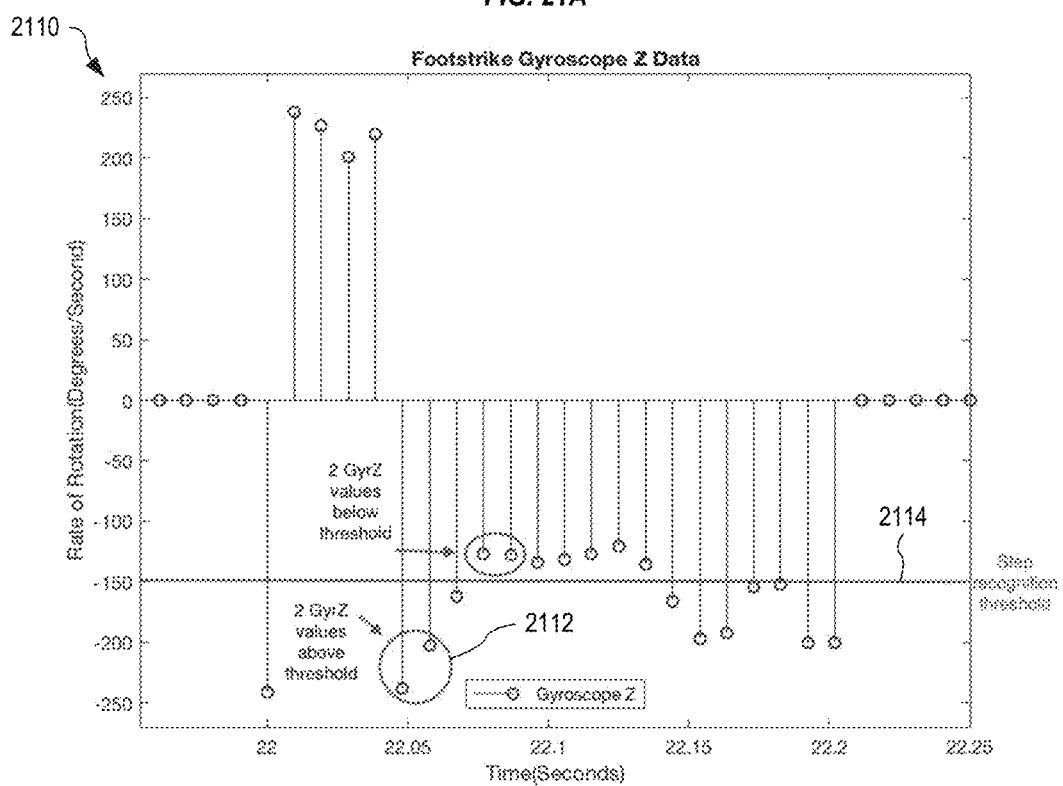
FIG. 21B is a graph showing example sensor data for GyrZ during contact of the foot with the ground.

In step 1812, method 1800 searches, in the vicinity of where the conditions in step 1804 or step 1808 occur, for negative GyrZ values with absolute values higher than the absolute value of the GyrZ threshold. FIG. 21B is a graph 2110 showing example sensor data 210 for GyrZ during contact of the foot with the ground, illustrating negative GyrZ values 2112 that have absolute values greater than the absolute value of GyrZ threshold 2114.

Step 1814 is a decision. If, in step 1814, method 1800 determines that the conditions of step 1812 were found, method 1800 continues with step 1818; otherwise method 1800 continues with step 1816. In step 1816, method 1800 determines that no foot strike is detected. Method 1800 then terminates. In step 1818, method 1800 determines that a foot strike is detected. Method 1800 then terminates. Method 1800 is invoked to detects foot strikes in subsequent sensor data 210.

Figure 19:
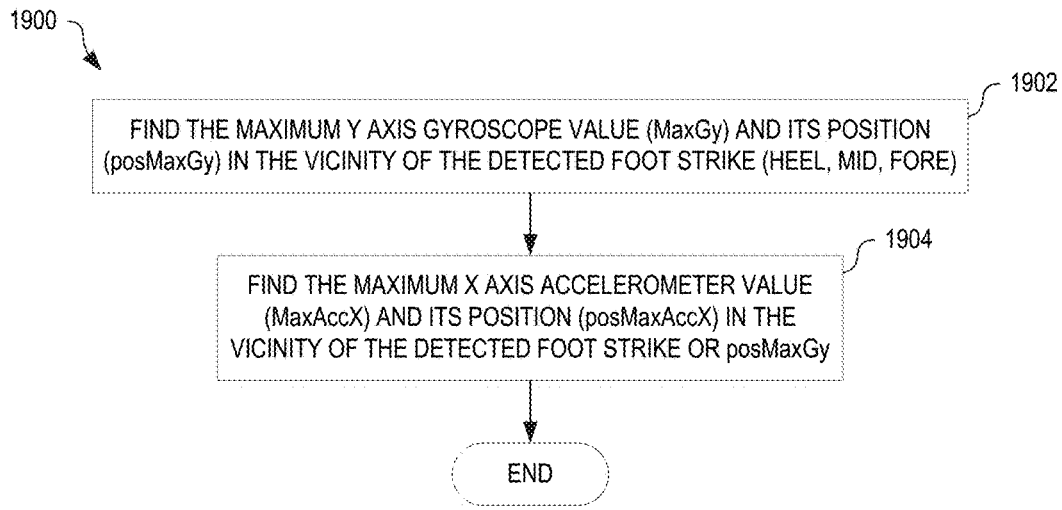
FIG. 19 is a flowchart illustrating one example method for max impact force detection, in an embodiment.

FIG. 19 is a flowchart illustrating one example method 1900 for max impact force detection. Method 1900 is implemented within max impact force algorithm 1604 of FIG. 16 for example, and may be invoked when a foot strike is determined in step 1818 of method 1800, FIG. 18.

Figure 21C:
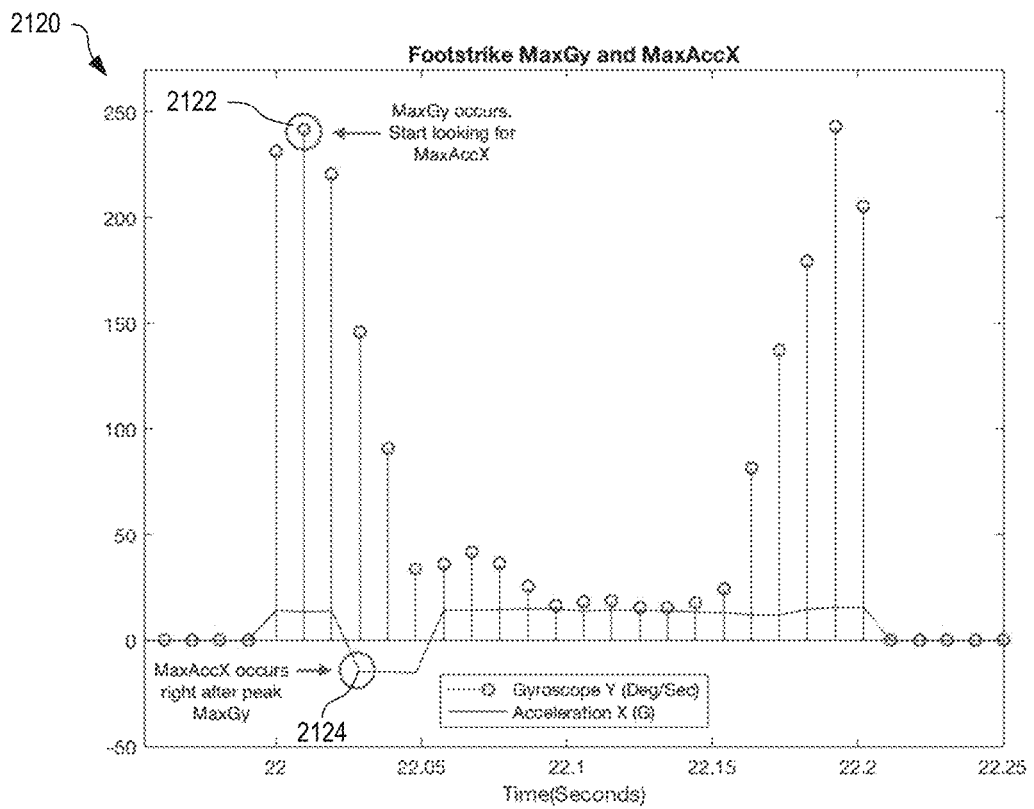
FIG. 21C is a graph showing example sensor data for GyrY and AccX during contact of the foot with the ground.

In step 1902, method 1900 finds the maximum Y axis gyroscope value (MaxGy) and its position (posMaxGy) in the vicinity of the detected foot strike (heel, mid, fore). FIG. 21C is a graph 2120 showing example sensor data 210 for GyrY and AccX during contact of the foot with the ground, illustrating MaxGy 2122.

In step 1904, method 1900 finds the maximum X axis accelerometer value (MaxAccX) and its position (posMaxAccX) in the vicinity of the detected foot strike or posMaxGy of step 1902. FIG. 21C also shows MaxAccX 2124 (negative value) occurring at a similar time to MaxGy 2122. It should be noted that there is always a max value for the gyroscope measuring in the Y axis right before there is a max value for the acceleration in the X axis. Algorithms included herein look for the MaxGy and record the position (e.g., in time) it occurred and then find the MaxAccX which is the vertical impact force felt by the runner.

Method 1900 then terminates.

Figure 20:
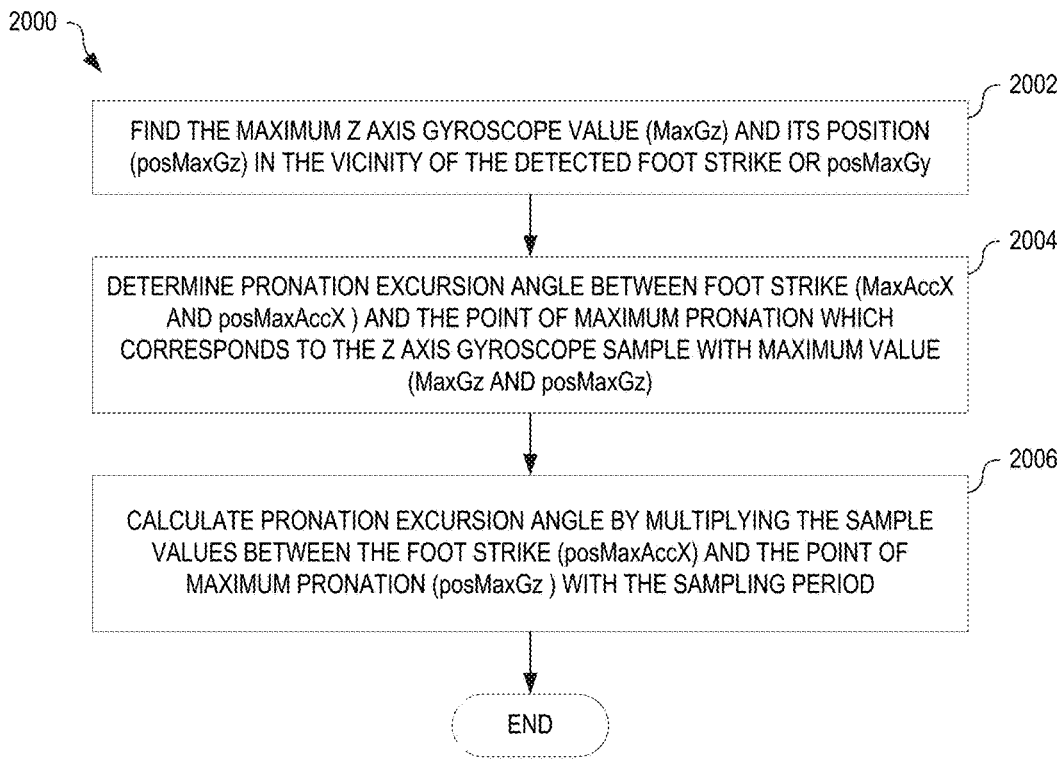
FIG. 20 is a flowchart illustrating one example method for pronation excursion angle detection, in an embodiment.

FIG. 20 is a flowchart illustrating one example method 2000 for pronation excursion angle detection. Method 2000 is implemented within pronation excursion angle algorithm 1606 of FIG. 16 for example and may be invoked by step 1818 of method 1800 when a foot strike is determined.

Figure 21D:
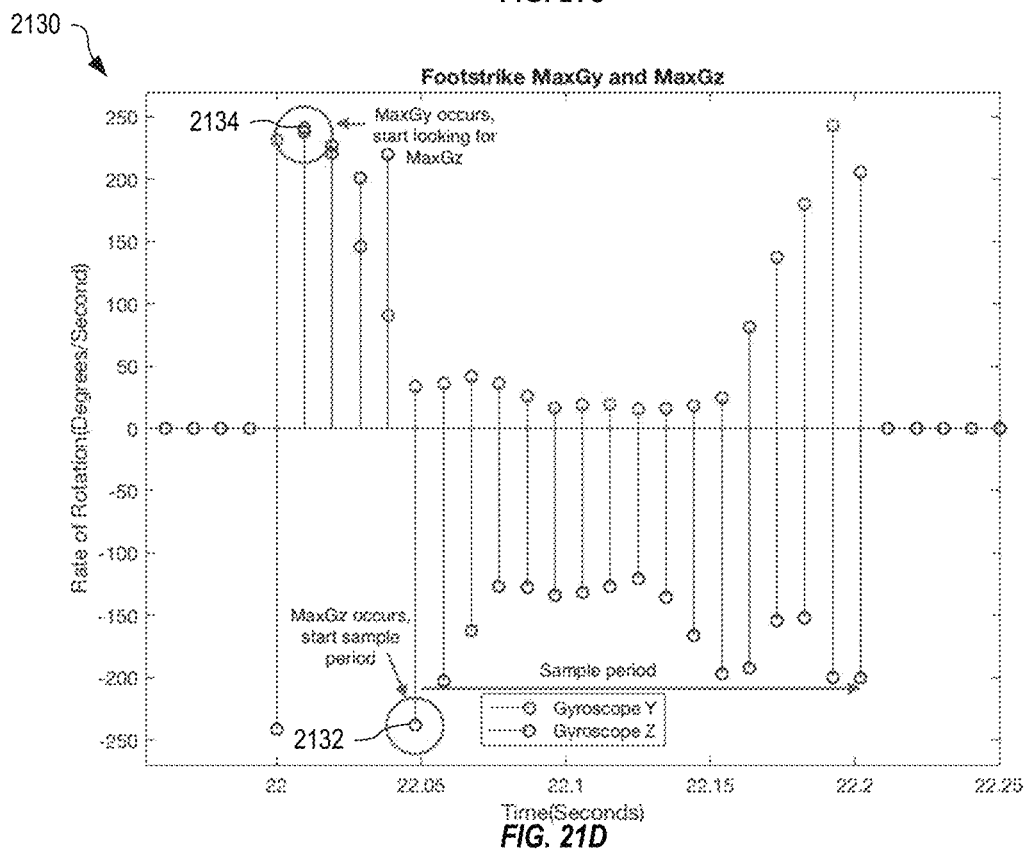
FIG. 21D is a graph showing example sensor data for GyrY and GyrZ during contact of the foot with the ground.

In step 2002, method 2000 find the maximum Z axis gyroscope value (MaxGz) and its position (posMaxGz) in the vicinity of the detected foot strike or posMaxGy of step 1902 of method 1900, FIG. 19. FIG. 21D is a graph 2130 showing example sensor data 210 for GyrY and GyrZ during contact of the foot with the ground, illustrating MaxGz 2132 and MaxGy 2134.

Figure 21E:
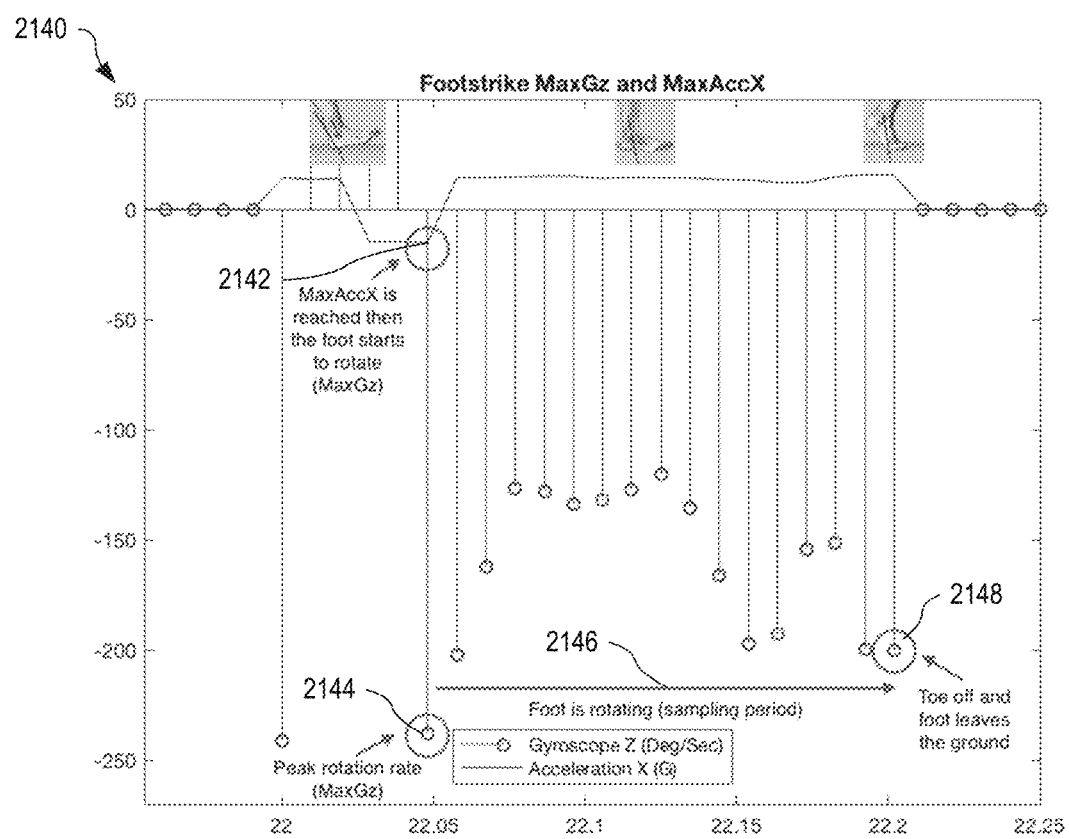
FIG. 21E is a graph showing example sensor data for GyrY and GyrZ during contact of the foot with the ground.

In step 1904, method 1900 determines pronation excursion angle between the foot strike (MaxAccX and posMaxAccX) and the point of maximum pronation which corresponds to the Z axis gyroscope sample with maximum value (MaxGz and posMaxGz). FIG. 21E is a graph 2140 showing example sensor data 210 for GyrY and GyrZ during contact of the foot with the ground, illustrating MaxAccX 2142 and MaxGz 2144.

In step 2006, method 2000 calculates the pronation excursion angle by multiplying the sample values between the foot strike (posMaxAccX) and the point of maximum pronation (posMaxGz) with the sampling period. FIG. 21E shows example sampling period 2146 between MaxGz 2144 and a point 2148 at which the toe leaves the ground. Since MaxGz is in units of degrees per second, in order to find the angle through which the foot traveled during the step, the algorithms herein uses the sampling period 2146, as seen in FIG. 21E, as bounds for the integration. The pronation excursion angle is found by integrating the values of the MaxGz over the sampling period. The numerical integration method used is Simpson's 1/3 method. Pronation angle is calculated for each step and then averaged over the whole run or session to be displayed to the user on communication device 120 for example.

Method 2000 then terminates.

FIGS. 22A, 22B, 23, and 24 show example sensor data 210 captured by foot strike monitor 102, illustrating how the algorithm used herein detect just the peak values and makes all other data zero, thereby making the peaks easier to identify.

Figure 22A:
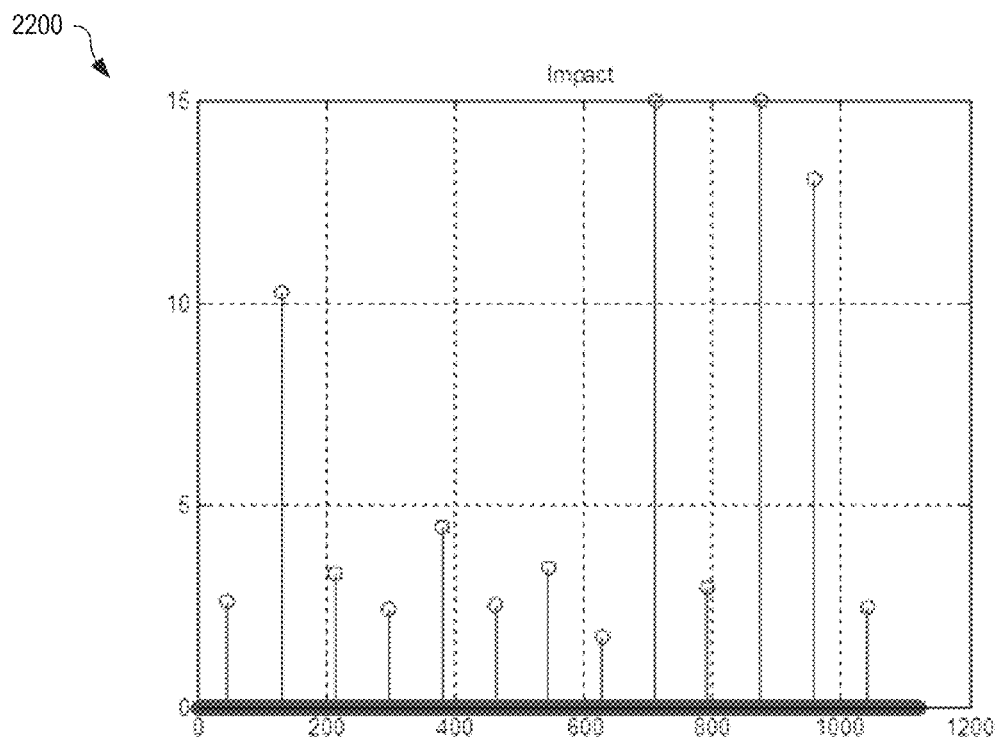
FIG. 22A is a graph showing example impact forces detected by the foot strike monitor of FIG. 1.

FIG. 22A is a graph 2200 showing example impact forces detected by foot strike monitor 102. In the example of FIG.

22A, the user is walking and values for impact are lower, as one would expect. Algorithms used herein may average peak values over an entire session (e.g., a walk) and published that average on communication device 120 for example.

Figure 22B:
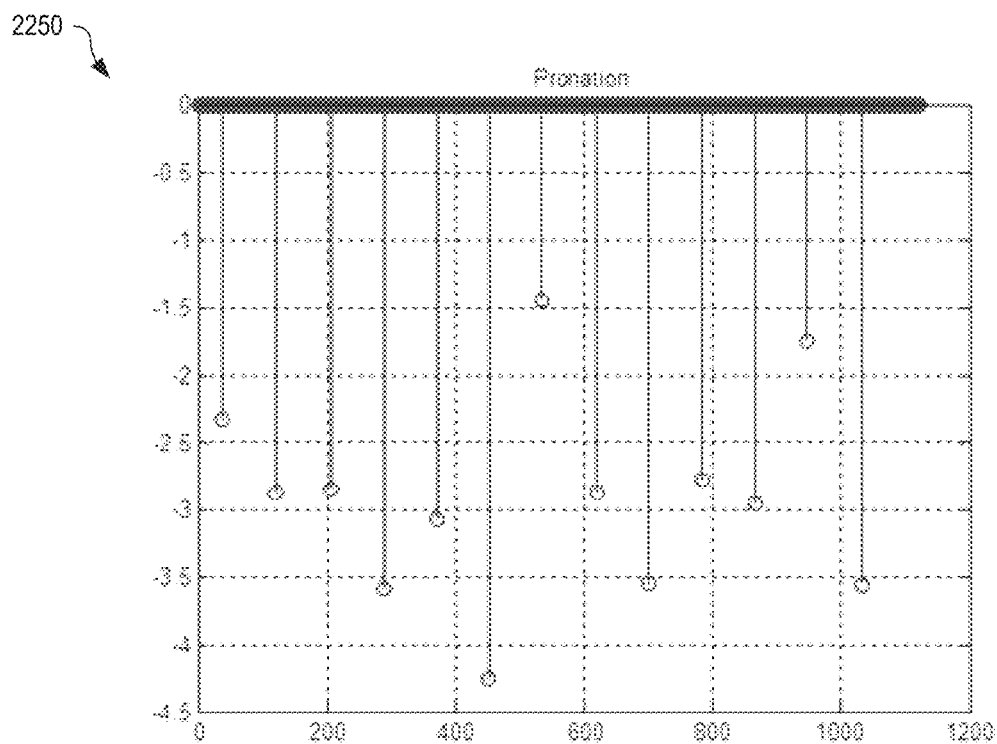
FIG. 22B is a graph showing example pronation detected by the foot strike monitor of FIG. 1.

FIG. 22B is a graph 2250 showing example pronation detected by foot strike monitor 102 for walking. The algorithms calculate the pronation by taking the MaxGz values and integrate over the sampling period to get a degree value for pronation. The pronation values are also low due to the fact that the person is walking, as compared to values expected for running.

Figure 23:
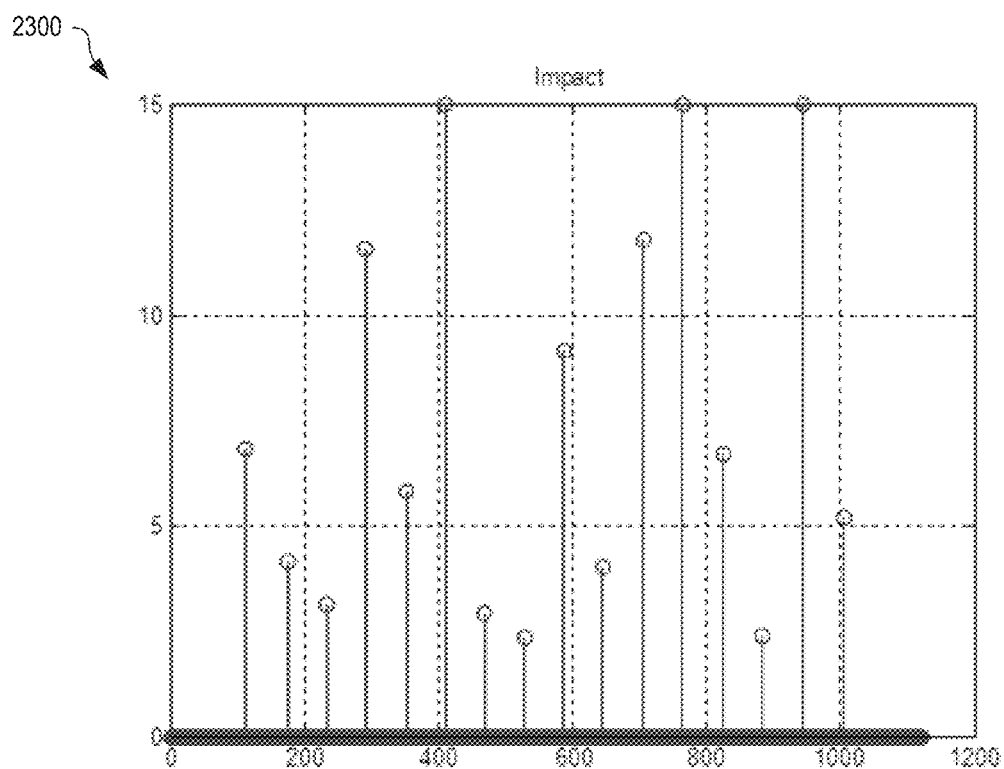
FIG. 23 is a graph showing example impact forces detected by the foot strike monitor of FIG. 1.

FIG. 23 is a graph 2300 showing example impact forces detected by foot strike monitor 102 for the user when running. The algorithm detects the peak values for running which vary more than the walking data and are higher in magnitude.

Figure 24:
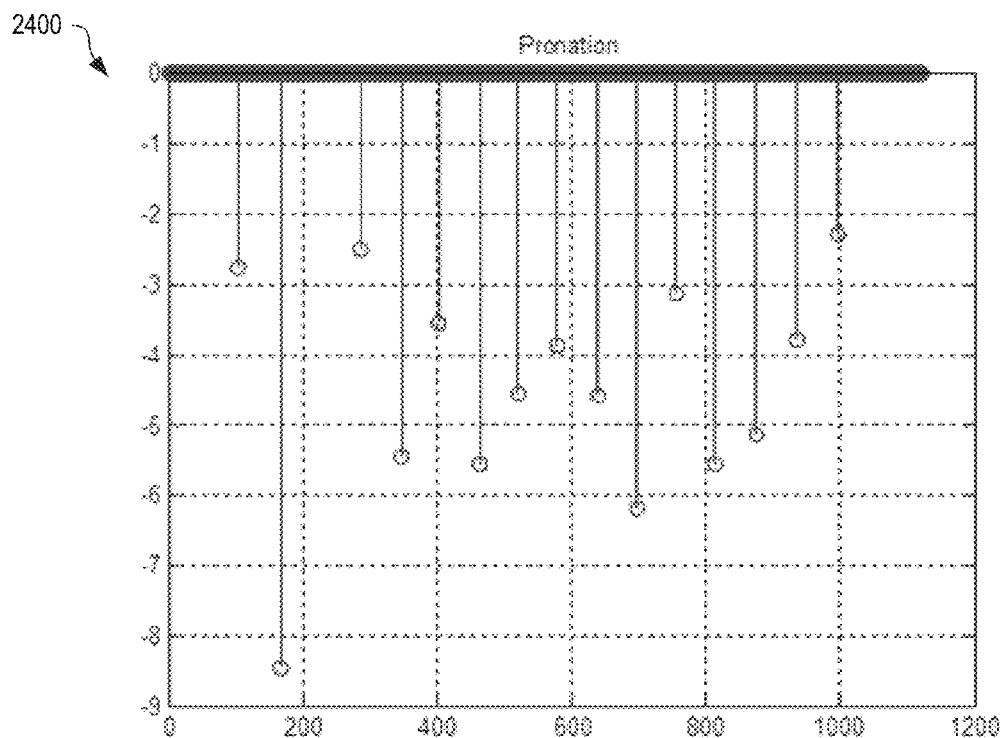
FIG. 24 is a graph showing example pronation detected by the foot strike monitor of FIG. 1.

FIG. 24 is a graph 2400 showing example pronation detected by foot strike monitor 102 for the user when running. The algorithm calculates the pronation as described above and, since the user is running, the values have increased due to the higher impact.

Figure 25:
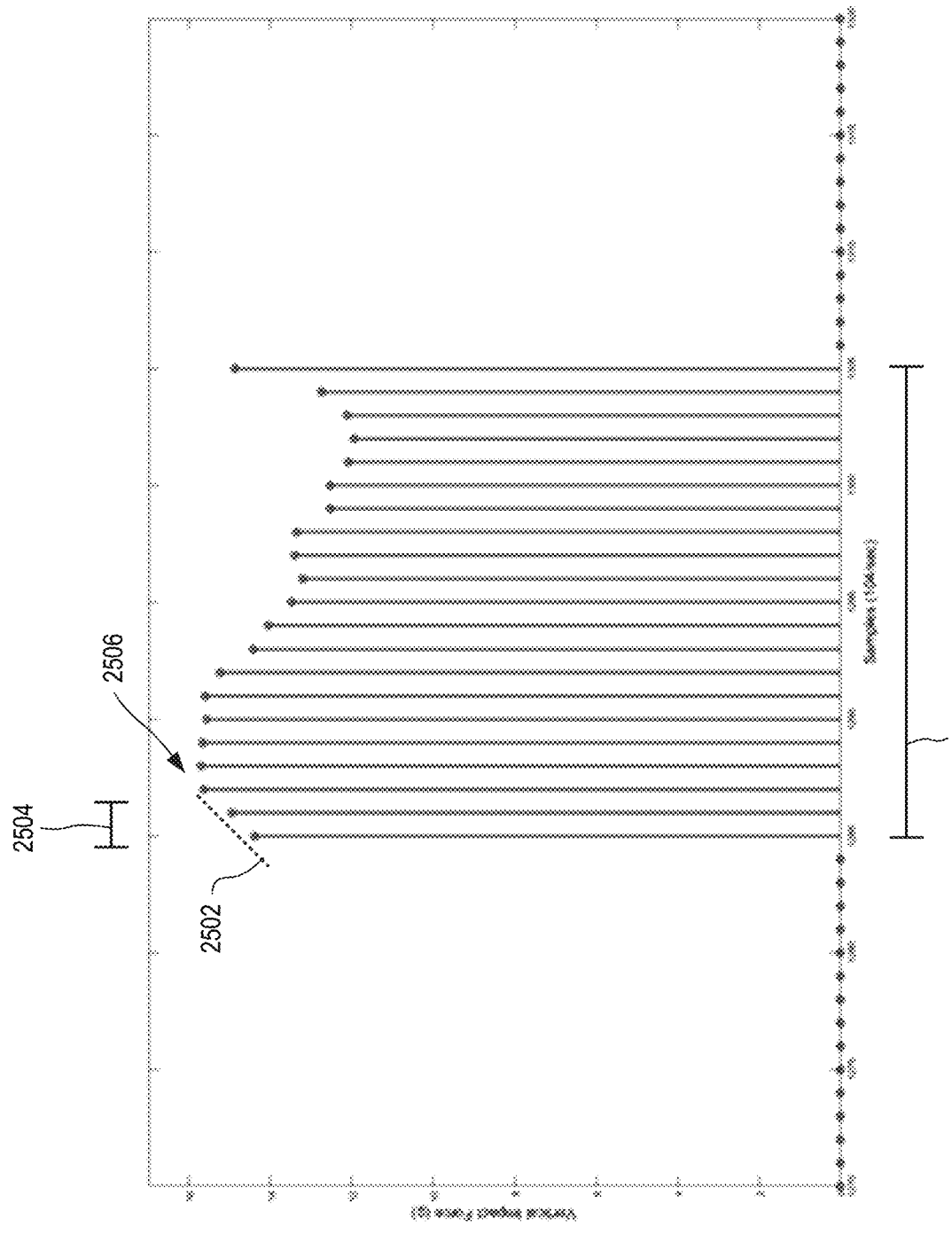
FIG. 25 shows an example impact graph illustrating time to reach peak impact within one step.

FIG. 25 shows an example impact graph 2500 illustrating time to reach peak impact in one step. Graph 2500 is a plot of peak impact on the vertical axis (Ax) for one step. The data is zeroed out before the peak in order to ensure the only the footstep is tracked and averaged and not the foot moving through the air. Period 2504 indicates that the peak impact at point 2506 occurs within 30 ms of the foot striking the ground. The foot reaches max acceleration quickly, as indicated by line 2502, and then the foot stops accelerating during the ground contact where the foot begins to rotate in (pronation) or out (supination). The final stage of the acceleration is when there is a dip in the acceleration and then a steep increase in which the foot is now accelerating during push-off of the foot from the ground. Line 2502 is the loading rate of the foot, indicative of how quickly the force goes into the body, and is factored into model 234. Ground contact time is around 200 ms as indicated by period 2508.

Once the data is put into the proper columns it is then analyzed for the key running metrics. The 16-*bit* two-complement data must be first converted to G's and degrees per second before it can be analyzed. The key metrics are steps, ground contact time, cadence, braking force, peak impact, rate of pronation, degree of pronation, acceleration in the xyz axis, and rate of rotation in the yz axis. The driver calls the ContactFunc which gives steps, ground contact time and cadence. The ForceFunc gives the average impact force and braking force and PronationFunc gives you the maximum angular rate and degree of rotation. The peak impact felt during a foot strike occurs in the first 30 ms and the pronation occurs in the first 130 ms and the total ground contact time is around 200 ms.

The Modelled Wear Factor

Figure 26:
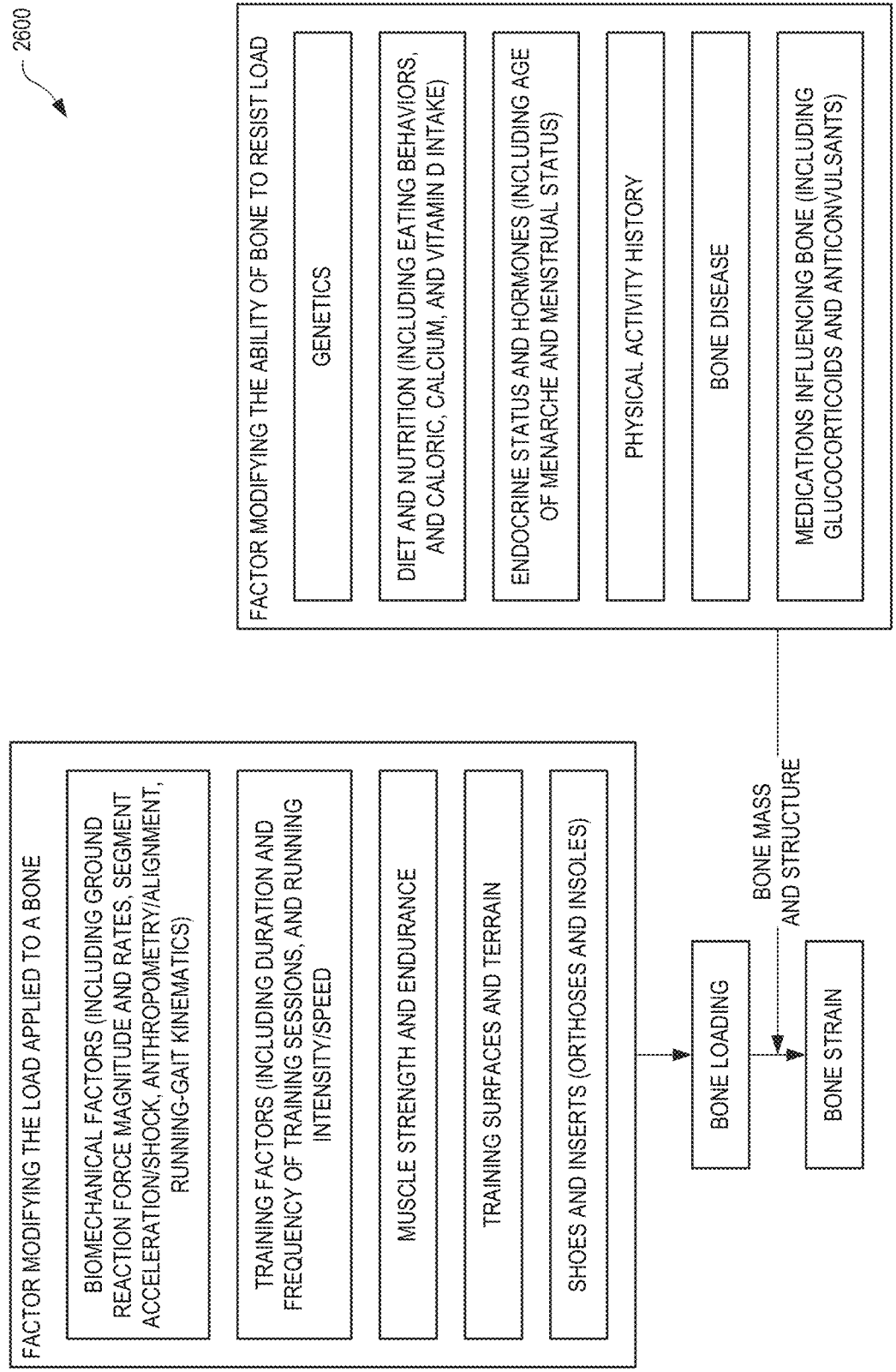
FIG. 26 is a schematic illustrating key factors that influence bone loading and bone strain when running.

FIG. 26 is a schematic illustrating key factors 2600 that influence bone loading and bone strain when running. These factors are incorporated into model 234 of FIG. 2 and used to determine shoe wear and predict a the lifetime of the shoe for the particular user. In one embodiment, each shoe is initially given an estimated lifetime of 400 miles. This lifetime is then adjusted by model 234 according to the following risk factors, shoe characteristics, and measured parameters of the user.

User information from runner profile 230, sensor data 210 collected from the user, and shoe characteristics 258 are evaluated and applied by model 234 to adjust the expected lifetime of the shoe as follows:

Injury History of the User
  0-5 injuries: Increase threshold 2%
  5-10 injuries: No deduction 0%
  10-15 injuries: Small Deduction −16%
  >15 injuries: medium deduction −2%
Age of the User
  Over 60 Large Deduction −3%
  50-60 Medium Deduction −2%
  40-50 Small Deduction −1%
  30-40 No Deduction 0%
  20-30 Small increase 1%
Activity Level of the User
  High Activity: Increase Threshold 2%
  Medium Activity: No deduction 0%
  Low Activity: Medium deduction −2%
  No Activity: Large deduction −3%
Years of Running
  0 Years: Large deduction −3%
  1 Years: medium −2%
  2 Years: small −1%
  3 Years: none 0%
Weight/Height of the User
  Height to weight ratio of health person at that age, height, gender
Foot Strike Type Made by the User
  Heel strike: Small deduction −1%
  Midfoot strike: Small increase 1%
Terrain Selected by the User
  Dirt: Medium increase 2%
  Mix: Small increase 1%
  Asphalt/concrete: medium deduction −2%
  Treadmill: Medium deduction −2%
Gender of the User
  Men: No deduction 0%
  Women: small deduction −1%
Shoe Characteristics
  Shoe characteristics 246 are applied to model 234, as follows:
  Thick sole: Increase 1%
  Minimal shoes: Medium deduction −2%
  Traditional shoe: None 0%
Alerts Based Upon Captured Data
  Muscle imbalance may be detected by comparing data from foot strike monitors 102 for each shoe 104.
  Discrepancy left and right (more that 10% difference between sides
  Ground contact time (Increase in ground contact time means fatigue)
  Pronation (Green if less than 10 degree, 11-20 Yellow, >20 Red)
  Cadence (Decrease in cadence means fatigue)
Nutrition
  Balanced diet (Increase 1%)
  Sleep (Increase 1%)
  Smoking alcohol (Decrease 3%)
Sensor Data
  Sensor data 210 is collected and stored within communication device 120 and may be processed to further adjust model 234. This data may also be sent to server 140 and used to determine adjustment for different types of user. For example, when a user has five consecutive runs (or a predefined number of steps) over a particular threshold (e.g., loading rate, peak impact, pronation rate, and/or pronation degree), an alarm is tripped and the user is alerted to the detected higher risk of injury and may be advised to replace shoes or change stride. This is in addition to model 234 and helps to ensure that there is no over-use injuries due wearing the wrong shoes. This alert indicates biomechanical issues that may be alleviated by correcting the shoe stability, strengthening exercises, stretching, foam rolling, and or gait retraining. These alerts occur when the sensor is reading values that are too high due to issues outside of the shoe, and may occur before the shoe is worn out. This alerts inform the user more about their running and any biomechanics/imbalances.

Loading Rate (Change in slope over time, dangerous when too steep) 50% increase in slope Peak impact (Magnitude over a period of time) <10 G good, 10-14 G Medium, >14 G Bad Rate of pronation (how fast the foot rotates before coming to a stop) (>300 degrees per second dangerous) (250 degree per second ok) (200 degrees per second good)

Pronation (Degree of rotation increases) 0-10 Ok, 11-20 Medium, >20 Bad

Supination (Degree of rotation increases) 0-(-10) Ok, -11-(-20) Medium, >(-20) Bad Shoe Profile One or more of the following characteristics of shoe 104 may be used to look-up and adjust model 234: Brand, Model, Men/Women, Size: US, Weight: Ounces, Road/trail shoe: Outsole, Heel Height: mm, Forefoot height: mm, Heel-toe Drop: mm, Width: Narrow, Regular, Wide, Extra wide, Material: Gel, plastic, boost, EVA foam, TPU foam (Boost), Stability material: Neutral, stability, motion control, Minimalist, Heel Counter: Plastic heel counter on upper of shoe, Flexibility: How easily it is to bend a shoe. Nike Free has high flexibility, Brooks Beast has low flexibility, Arch support: High, medium, low arch height in shoe, and Footstrike: Heel, Midfoot, Forefoot.

Community

In one embodiment, server 140 may implement a communicate database where a user may input how they feel about the shoe wear and when they actually replace their shoes compared to when the model recommended to replace their shoes. This community database may allow users to read reviews on and provide reviews for shoes based upon characteristics and measurements determined by foot strike monitor 102.

In one embodiment, software 136 running on communication device 130 may automatically recognize and log exercise sessions performed by the user. For example, based upon sensor data 210, software 136 may utilize model 234 to determine when the user is running, walking, and stationary, and may determine a map of activity throughout the day as an accurate activity log.

Other Uses

Foot strike analyzer 102 and/or software 136 may have other uses. For example, foot strike analyzer 102 and/or software 136 may be used to check that safety footwear is functioning properly. For example, foot strike monitor 102 may be configured with firemen's boots and used to ensure that the boots have the correct stiffness and/or non-slip grip. For example, as a type of shoe, the fireman's boot may have defined thresholds for performance that may be evaluated by software 136.

Foot strike analyzer 102 may be configured with other sensors (e.g., magnetometers) that may detect magnetic strips positioned around a building, where each magnetic strip may be encoded such that foot strike monitor 102 may determine its location when detecting the strip.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A system for analyzing foot strikes, comprising:
   a foot strike monitor, configurable with a running shoe, for detecting movement of a foot of a runner within the running shoe, said foot strike monitor further comprising:
   at least three sensors for measuring foot motion around three orthogonal axes;
   a communications interface;
   a first processor; and
   a memory forming a buffer for storing detected movement data from the at least three sensors; and
   a communication device for receiving and processing data from the foot strike monitor, said communication device further comprising:
   a display;
   a second processor; and
   memory storing non-transitory computer-readable instructions that, when executed by the second processor, control the second processor to:
   receive the detected movement data from the buffer in the foot strike monitor;
   search the detected movement data from a first sensor of the at least three sensors to find at least two successive values that meet a condition indicating a foot strike;
   find a value in the detected movement data from a second sensor of the at least three sensors in the vicinity of the foot strike that indicates a maximum impact force of the foot strike;
   find a value in the detected movement data from a third sensor of the at least three sensors in the vicinity of the foot strike that indicates a pronation excursion angle; and
   displaying at least one impact force and protation excursion angle,
   model wear on the running shoe based upon characteristics of the runner and characteristics of the running shoe to determine a performance of the running shoe, the characteristics of the runner including at least one of the runner's age, activity level, running experience, height, height-to-weight ratio, gender, diet, sleep habits, and alcohol consumption;
   predict, based on the modelled wear, a date when the performance of the running shoe will fall below a defined threshold; and
   alert the runner to the predicted date.

2. The system of claim 1, the second processor further configured to process the detected movement to detect and record a traumatic event based upon acceleration and rotation of the runner's foot.

3. The system of claim 1, wherein the at least one characteristic of the runner includes both the runner's age and the runner's height-to-weight ratio.

4. A method for analyzing foot strikes, comprising:
   receiving a runner profile defining characteristics of a user and a shoe type of shoes;
   retrieving shoe characteristics based upon the shoe type;
   configuring a model of shoe wear based upon both the runner profile and the shoe characteristics, the runner profile including at least one of the runner's age, activity level, running experience, height, height-to-weight ratio, gender, diet, sleep habits, and alcohol consumption;

receiving sensor data from at least three sensors indicative of movement of a runner's foot from a foot strike monitor configured with the shoes;

search the sensor data from a first sensor of the at least three sensors to find at least two successive values that meet a condition indicating a foot strike;

find a value in the sensor data from a second sensor of the at least three sensors in the vicinity of the foot strike that indicates a maximum impact force of the foot strike;

find a value in the sensor data from a third sensor of the at least three sensors in the vicinity of the foot strike that indicates a pronation excursion angle; and processing the maximum impact force and pronation excursion angle through the model to determine a user's expected lifetime for the shoes; and indicating the user's expected lifetime to the user.

5. The method of claim 4, the shoe characteristics defining a manufacturer's expected lifetime of the shoes, wherein the model adjusts the manufacturer's expected lifetime to determine the user's expected lifetime based upon the runner profile, the sensor data, and the shoe characteristics.

6. The method of claim 5, wherein the runner profile defining characteristics of the user includes a health of the user, activity of the user, and terrain information.

7. The method of claim 5, the user's expected lifetime of the shoes being further adjusted based upon subsequently received sensor data indicative of a running style of the user.

8. The method of claim 5, the user's expected lifetime of the shoes being further adjusted based upon subsequently received sensor data indicative of protection provided by the shoes.

9. The method of claim 4, further comprising:

detecting, within the sensor data, reductions in cushioning and support provided by the shoes; and alerting the user to danger resulting from the reductions in cushioning and support.

10. The method of claim 9, the step of detecting comprising detecting reductions in cushioning and support for a predefined number of occurrences.

11. The method of claim 9, the step of detecting comprising detecting one or both of increased peak strike force and increased pronation.

12. The method of claim 4, wherein the runner profile includes both the runner's age and the runner's height-to-weight ratio.

* * * * *